US011511121B2

(12) United States Patent
Sit et al.

(10) Patent No.: US 11,511,121 B2
(45) Date of Patent: Nov. 29, 2022

(54) STIMULATION APPARATUS

(71) Applicant: Nalu Medical, Inc., Carlsbad, CA (US)

(72) Inventors: Ji-Jon Sit, Carlsbad, CA (US); Daniel M. Pivonka, Palo Alto, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 0 days.

(21) Appl. No.: 16/453,917

(22) Filed: Jun. 26, 2019

(65) Prior Publication Data
US 2020/0139138 A1    May 7, 2020

Related U.S. Application Data

(63) Continuation of application No. PCT/US2017/068803, filed on Dec. 28, 2017.
(Continued)

(51) Int. Cl.
*A61N 1/372* (2006.01)
*A61N 1/05* (2006.01)
(Continued)

(52) U.S. Cl.
CPC .......... *A61N 1/37252* (2013.01); *A61N 1/05* (2013.01); *A61N 1/08* (2013.01); *A61N 1/378* (2013.01);
(Continued)

(58) Field of Classification Search
CPC ........... A61N 1/37229; A61N 1/37235; A61N 1/3787; A61N 1/37247; A61N 1/37264;
(Continued)

(56) References Cited

U.S. PATENT DOCUMENTS 7,737,905 B1 *  6/2010  Meloling ................. H01Q 7/08
                                                       343/788
8,504,138 B1    8/2013  Pivonka et al.
(Continued)

FOREIGN PATENT DOCUMENTS

WO    WO-2014071079 A1    5/2014
WO    WO-2014205129 A1    12/2014
(Continued)

OTHER PUBLICATIONS

EP17887576.1 European Search Report dated Oct. 9, 2020.

*Primary Examiner* — Eric D. Bertram
(74) *Attorney, Agent, or Firm* — Cooley LLP

(57) ABSTRACT

Provided is a medical apparatus for a patient comprising an external system and an implantable system. The external system can be configured to transmit one or more transmission signals, each transmission signal comprising at least power or data. The implantable system can be configured to receive the one or more transmission signals from the external system. The external system comprises a first external device comprising at least one external antenna configured to transmit a first transmission signal to the implantable system. The implantable system comprises a first implantable device comprising at least one implantable antenna configured to receive the first transmission signal from the first external device. At least one of the external antenna or implantable antenna comprises an antenna assembly comprising: at least one transmitting/receiving antenna; and at least one shielding element positioned between the at least one transmitting/receiving antenna and an interfering component.

22 Claims, 12 Drawing Sheets

Related U.S. Application Data

(60) Provisional application No. 62/441,056, filed on Dec. 30, 2016.

(51) Int. Cl.
  *A61N 1/08* (2006.01)
  *A61N 1/378* (2006.01)

(52) U.S. Cl.
  CPC ........ *A61N 1/37229* (2013.01); *A61N 1/3787* (2013.01); *A61N 1/37235* (2013.01)

(58) Field of Classification Search
  CPC .......... A61N 1/36; A61N 1/362; A61N 1/372; A61N 1/36062; A61N 1/08; H02J 50/10; H04B 5/0093; H04B 5/0031; H04B 5/0037
  See application file for complete search history.

(56) References Cited

U.S. PATENT DOCUMENTS

| | | | |
|---|---|---|---|
| 8,634,928 | B1 | 1/2014 | O'Driscoll et al. |
| 9,433,750 | B2 | 9/2016 | Pivonka et al. |
| 10,238,872 | B2 | 3/2019 | Pivonka et al. |
| 10,320,232 | B2 | 6/2019 | Pivonka et al. |
| 10,335,596 | B2 | 7/2019 | Yakovlev et al. |
| 10,411,760 | B2 | 9/2019 | Yakovlev et al. |
| 10,644,539 | B2 | 5/2020 | Pivonka et al. |
| 2003/0055406 | A1* | 3/2003 | Lebel ................ A61B 5/14532 604/891.1 |
| 2004/0119552 | A1* | 6/2004 | Wray ..................... H01P 1/26 333/22 R |
| 2006/0074450 | A1 | 4/2006 | Boveja et al. |
| 2006/0247738 | A1* | 11/2006 | Schmeling ........... A61N 1/3787 607/61 |
| 2010/0168817 | A1* | 7/2010 | Yamamoto .............. H01Q 3/26 607/60 |
| 2011/0234155 | A1* | 9/2011 | Chen ...................... H02J 50/70 320/108 |
| 2012/0197352 | A1 | 8/2012 | Carbunaru et al. |
| 2013/0215979 | A1 | 8/2013 | Yakovlev et al. |
| 2014/0163338 | A1* | 6/2014 | Roesicke ............. A61B 5/0031 600/309 |
| 2015/0335285 | A1 | 11/2015 | Poon et al. |
| 2016/0087687 | A1* | 3/2016 | Kesler .................. H04B 5/0037 307/104 |
| 2016/0331956 | A1 | 11/2016 | Yakovlev et al. |
| 2018/0028824 | A1 | 2/2018 | Pivonka et al. |
| 2018/0090971 | A1* | 3/2018 | Graham ................ H01F 27/288 |
| 2018/0256906 | A1 | 9/2018 | Pivonka et al. |
| 2018/0368875 | A1 | 12/2018 | Castillo et al. |
| 2019/0001139 | A1 | 1/2019 | Mishra et al. |
| 2019/0009097 | A1 | 1/2019 | Hartley et al. |
| 2019/0151659 | A1 | 5/2019 | Mishra et al. |
| 2019/0269913 | A1 | 9/2019 | Pivonka et al. |
| 2019/0374776 | A1 | 12/2019 | Mishra et al. |
| 2020/0101291 | A1 | 4/2020 | Yakovlev et al. |
| 2020/0204209 | A1 | 6/2020 | Yakovlev et al. |
| 2020/0222000 | A1 | 7/2020 | Poon et al. |
| 2020/0306528 | A1 | 10/2020 | Linden et al. |
| 2020/0398058 | A1 | 12/2020 | Pivonka et al. |
| 2021/0099015 | A1 | 4/2021 | Pivonka et al. |
| 2021/0196957 | A1 | 7/2021 | Yakolev et al. |

FOREIGN PATENT DOCUMENTS

| | | | | |
|---|---|---|---|---|
| WO | WO-2015139053 A1 * | 9/2015 | ......... | A61N 1/36062 |
| WO | WO-2015196164 A2 * | 12/2015 | ............. | A61N 2/008 |
| WO | WO-2016127130 A1 | 8/2016 | | |
| WO | WO-2016205373 A1 * | 12/2016 | ............. | H02J 50/10 |
| WO | WO-2017044904 A1 | 3/2017 | | |
| WO | WO-2017142948 A1 | 8/2017 | | |
| WO | WO-2017165410 A1 | 9/2017 | | |
| WO | WO-2017205675 A1 | 11/2017 | | |
| WO | WO-2018017463 A1 | 1/2018 | | |
| WO | WO-2018126062 A1 | 7/2018 | | |
| WO | WO-2018156953 A1 | 8/2018 | | |
| WO | WO-2018208992 A1 | 11/2018 | | |
| WO | WO-2021003439 | 1/2021 | | |
| WO | WO-2021067873 | 4/2021 | | |
| WO | WO-2021/133947 | 7/2021 | | |

\* cited by examiner

STIMULATION APPARATUS

CROSS REFERENCE

This application is a continuation of PCT Application No. PCT/US17/68803, filed Dec. 28, 2017; which claims priority to U.S. Provisional Patent Application Ser. No. 62/441,056, filed Dec. 30, 2016; the entire contents of which are incorporated herein by reference in their entirety for all purposes.

DESCRIPTION OF THE INVENTION

Related Applications

This application is related to: U.S. patent application Ser. No. 14/975,358, titled "Method and Apparatus for Minimally Invasive Implantable Modulators", filed Dec. 18, 2015; U.S. patent application Ser. No. 15/264,864, titled "Method and Apparatus for Versatile Minimally Invasive Neuromodulators", filed Sep. 14, 2016; International PCT Patent Application Serial Number PCT/US2015/036821, titled "Method and Apparatus for Neuromodulation Treatments of Pain and Other Conditions", filed Jun. 19, 2015; International PCT Patent Application Serial Number PCT/US2016/016888, titled "Medical Apparatus Including an Implantable System and an External System", filed Feb. 5, 2016; International PCT Patent Application Serial Number PCT/US2016/051177, titled "Apparatus for Peripheral or Spinal Stimulation", filed Sep. 9, 2016; U.S. Provisional Patent Application Ser. No. 62/341,418, titled "Methods and Systems for Insertion and Fixation of Implantable Devices", filed May 25, 2016; U.S. Provisional Patent Application Ser. No. 62/297,679, titled "Apparatus with Enhanced Stimulation Waveforms", filed Feb. 19, 2016; U.S. Provisional Patent Application Ser. No. 62/417,907, titled "Apparatus with Enhanced Stimulation Waveforms", filed Nov. 4, 2016; U.S. Provisional Patent Application Ser. No. 62/311,297, titled "Devices and Methods for Positioning External Devices in Relation to Implanted Devices", filed Mar. 21, 2016; and U.S. Provisional Patent Application Ser. No. 62/363,742, titled "Methods and Systems for Treating Pelvic Disorders and Pain Conditions", filed Jul. 18, 2016; the content of each of which is incorporated herein by reference in its entirety for all purposes.

FIELD OF THE INVENTION

The present invention relates generally to medical apparatus for a patient, and in particular, to stimulation apparatuses that operate with improved efficiency and performance.

BACKGROUND OF THE INVENTION

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g., to treat pain). Most implants are relatively large devices with batteries and long conduits, such as implantable leads configured to deliver electrical energy or implantable tubes (i.e., catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices, and methods that provide one or more implantable devices and are designed to provide enhanced treatment of pain and other enhanced benefits.

SUMMARY

Medical apparatus of the present inventive concepts can include antenna assemblies that include one or more antennas and one or more shielding elements.

According to an aspect of the inventive concepts, a medical apparatus for a patient comprises an external system and an implantable system. The external system can be configured to transmit one or more transmission signals, each transmission signal comprising at least power or data. The implantable system can be configured to receive the one or more transmission signals from the external system. The external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and/or an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable functional element configured to interface with the patient; an implantable controller configured to control the at least one implantable functional element; an implantable energy storage assembly configured to provide power to an element selected from the group consisting of: the at least one implantable functional element; the implantable controller; the implantable receiver; and combinations thereof and/or an implantable housing surrounding at least the implantable controller and the implantable receiver. At least one of the external antenna or implantable antenna comprises an antenna assembly comprising: at least one transmitting/receiving antenna; and at least one shielding element positioned between the at least one transmitting/receiving antenna and an interfering component.

In some embodiments, the shielding element comprises multiple shielding elements.

In some embodiments, the shielding element comprises a material selected from the group consisting of: high permeability material; low magnetic loss tangent material; low conductivity material; and combinations thereof. The shield can comprise a magnetic permeability (u') of greater than or equal to 40. The shield can comprise a magnetic loss tangent (u"/u') of less than or equal to 0.025. The shield can comprise a conductivity of less than or equal to 1e-3 S/m. The shield can comprise a conductivity of less than or equal to 1e−5 S/m. The at least one transmitting/receiving antenna can be configured to deliver transmissions with an operating frequency above 1 Mhz. The at least one transmitting/receiving antenna can be configured to deliver transmissions with an operating frequency above 10 Mhz.

In some embodiments, the shielding element comprises high frequency ferrite. The at least one transmitting/receiving antenna is configured to deliver transmissions with an operating frequency above 1 Mhz, or above 10 Mhz, such as at an operating frequency of approximately 40.68 MHz. These transmissions can be performed at a power level between 10 mW and 4 W, such as a power level between 10 mW and 400 mW.

In some embodiments, the shielding element comprises a material selected from the group consisting of: electromagnetically absorptive material; RF absorptive material; conductive material; and combinations thereof.

In some embodiments, the shielding element is configured to shield the at least one transmitting/receiving antenna from interfering components.

In some embodiments, the shielding element is configured to shield at least a portion of the environment surrounding the at least one transmitting/receiving antenna. The shielding element can be configured to shield the environment on the side of the shield opposite the at least one transmitting/receiving antenna. The shielding element can be configured to reduce electromagnetic shielding and/or filtering requirements of the apparatus. The shielding element can comprise a material selected from the group consisting of: electromagnetically absorptive material; RF absorptive material; conductive material; and combinations thereof.

In some embodiments, the interfering component comprises at least one electrically conductive component.

In some embodiments, the interfering component comprises at least one metallic component.

In some embodiments, the interfering component comprises at least one component that would otherwise cause an effect selected from the group consisting of: undesired loading; undesired coupling; a parasitic effect; and combinations thereof.

In some embodiments, the interfering component comprises at least one component to which transmissions from the at least one transmitting/receiving antenna would otherwise cause a deleterious effect.

In some embodiments, the apparatus further comprises at least one space-providing element. The at least one space-providing element can be positioned between the at least one transmitting/receiving antenna and the shield. The at least one space-providing element can comprise a gap. The at least one space-providing element can comprise a thickness between 0.01 mm and 5 mm, or a thickness between 0.25 mm and 1 mm. The at least one space-providing element can comprise a non-conductive dielectric material. The at least one space-providing element can comprise a material selected from the group consisting of: glass reinforced epoxy laminate; acetal; and combinations of one or more of these. The at least one space-providing element comprises a dielectric loss tangent of less than or equal to 0.05, less than or equal to 0.02; and/or less than or equal to 0.005. The at least one space-providing element comprises multiple spacers. A first space-providing element can be positioned on a first side of the at least one transmitting/receiving antenna and a second space-providing element can be positioned on a second side of the at least one transmitting/receiving antenna.

In some embodiments, the external device comprises a first housing and a separate second housing. The first housing can surround at least the transmitting/receiving antenna, the second housing can surround at least the external transmitter, the first housing can be constructed and arranged for placement proximate the patient's skin, and the second housing can be constructed and arranged for placement relatively away from the patient's skin.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE DRAWINGS

Figure 1:
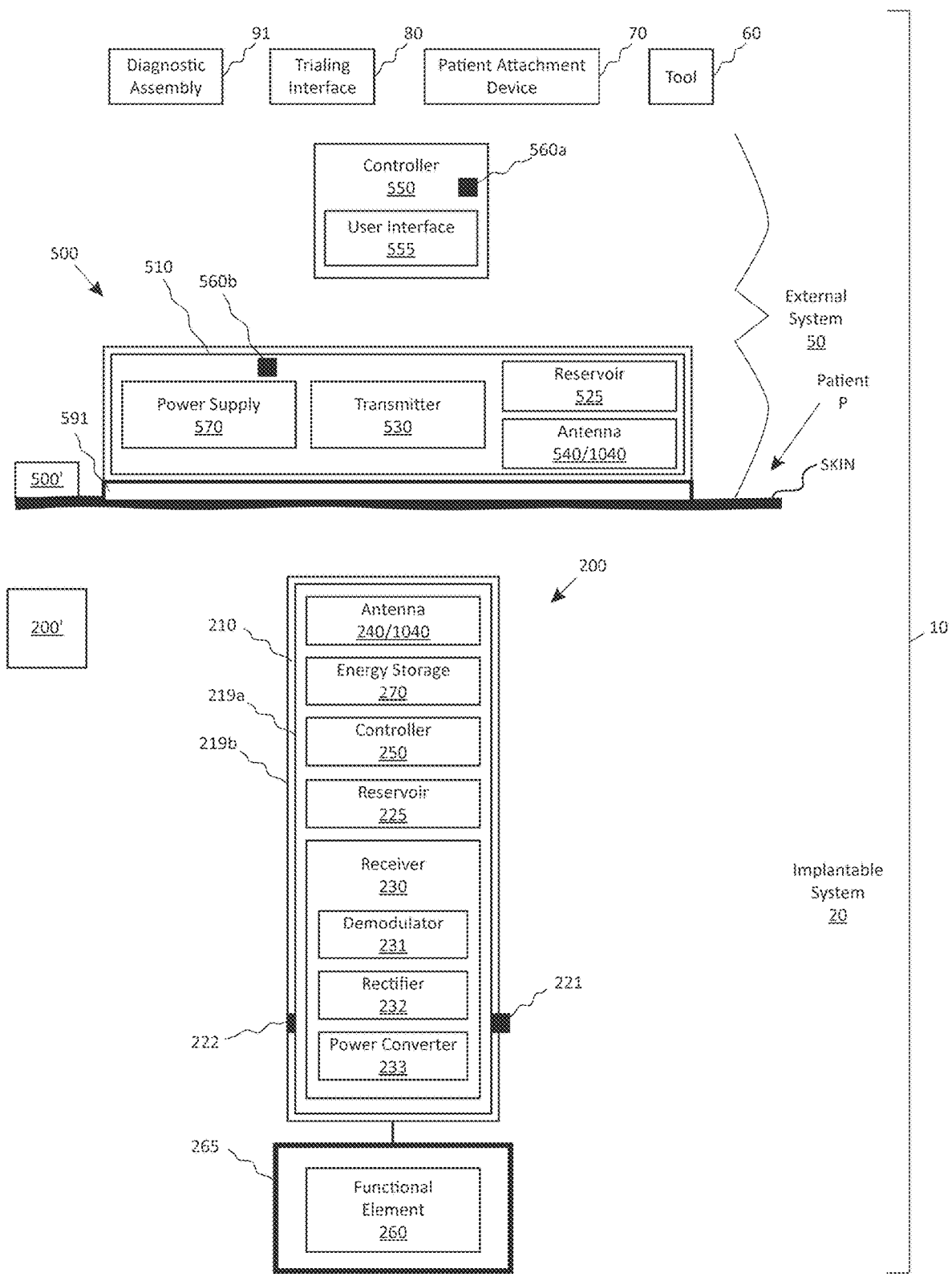
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections; these limitations, elements, components, regions, layers and/or sections should not be limited by these terms. These terms are only used to distinguish one limitation, element, component, region, layer or section from another limitation, element, component, region, layer, or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.). A first component (e.g., a device, assembly, housing or other component) can be "attached", "connected" or "coupled" to another component via a connecting filament (as defined below). In some embodiments, an assembly comprising multiple components connected by one or more connecting filaments is created during a manufacturing process (e.g., pre-connected at the time of an implantation procedure of the system of the present inventive concepts). Alternatively or additionally, a connecting filament can comprise one or more connectors (e.g., a connectorized filament comprising a connector on one or both ends), and a similar assembly can be created by a user (e.g., a clinician) operably attaching the one or more connectors of the connecting filament to one or more mating connectors of one or more components of the assembly.

It will be further understood that when a first element is referred to as being "in", "on", and/or "within" a second element, the first element can be positioned: within an internal space of the second element, within a portion of the second element (e.g., within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

As used herein, the term "proximate" shall include locations relatively close to, on, in and/or within a referenced component or other location.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g., based on the size of the electrode). In some configurations, a transducer converts an electrical signal into any output, such light (e.g., a transducer comprising a light emitting diode or light bulb), sound (e.g., a transducer comprising a piezo crystal configured to deliver ultrasound energy), pressure, heat energy, cryogenic energy, chemical energy; mechanical energy (e.g., a transducer comprising a motor or a solenoid), magnetic energy, and/or a different electrical signal (e.g., a Bluetooth or other wireless communication element). Alternatively or additionally, a transducer can convert a physical quantity (e.g., variations in a physical quantity) into an electrical signal. A transducer can include any component that delivers energy and/or an agent to tissue, such as a transducer configured to deliver one or more of: electrical energy to tissue (e.g., a transducer comprising one or more electrodes); light energy to tissue (e.g., a transducer comprising a laser, light emitting diode and/or optical component such as a lens or prism); mechanical energy to tissue (e.g., a transducer comprising a tissue manipulating element); sound energy to tissue (e.g., a transducer comprising a piezo crystal); thermal energy to tissue (e.g., heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal. A transmission signal can comprise a modulated signal (e.g., a frequency modulated signal) which includes a carrier frequency (also referred to as an "operating frequency" herein).

The term "data signal" where used herein is to be taken to include a transmission signal including at least data. For example, a data signal can comprise a transmission signal including data and sent from a component external to the patient and one or more components implanted in the patient. Alternatively, a data signal can comprise a transmission signal including data sent from an implanted component to one or more components external to the patient. A data signal can comprise a radiofrequency signal including data (e.g., a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "connection", "connected", "connecting" and the like, where used herein, are to be taken to include any type of connection between two or more components. The connection can include an operable connection which allows multiple connected components to operate together such as to transfer information, power and/or material (e.g., an agent to be delivered) between the components. An operable connection can include a physical connection, such as a physical connection including one or more wires, optical fibers, wave guides, tubes such as fluid transport tubes and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g., clinician or other user-attachable connectors) for operably connecting that component to a mating connector (e.g., of the same or different component).

The terms "stimulation parameter", "stimulation signal parameter" or "stimulation waveform parameter" where used herein can be taken to refer to one or more parameters of a stimulation waveform (also referred to as stimulation signal). Applicable stimulation parameters of the present inventive concepts shall include but are not limited to: amplitude (e.g., amplitude of voltage and/or current); average amplitude; peak amplitude; frequency; average frequency; period; phase; polarity; pulse shape; a duty cycle parameter (e.g., frequency, pulse width and/or off time); inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g., the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an inter-phase gap can be present within a single pulse. The term "quiescent period" where used herein can refer to a period of time during which zero energy or minimal energy is delivered (e.g., insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can be a human or other mammalian patient. The medical apparatus can comprise a stimulation apparatus. The medical apparatus can comprise an implantable system and an external system. The implantable system can comprise one or more similar and/or dissimilar implantable devices. Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements. An implantable functional element can be configured to interface with the patient (e.g., interface with tissue of the patient or interface with any patient location). Alternatively or additionally, an implantable functional element can interface with a portion of an implantable device (e.g., to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g., patient physiologic or patient environment information).

Each implantable device can comprise an implantable controller configured to control (e.g., modulate power to, send a signal to and/or receive a signal from) the one or more implantable functional elements. In some embodiments, an implantable controller of a first implantable device is configured to control one or more other implantable devices. Each implantable device can comprise an implantable energy storage assembly configured to provide power to the implantable controller (e.g., a controller comprising a stimulation waveform generator), the implantable receiver and/or the one or more implantable functional elements. In some embodiments, an implantable energy storage assembly is further configured to provide power to an assembly that transmits signals via the implantable antenna (e.g., when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be tethered (e.g., electrically tethered) to the implantable housing. In some embodiments, one or more implantable functional elements are positioned on an implantable lead, such as a flexible lead mechanically fixed or attachable to the implantable housing and operably connected (e.g., electrically, fluidly, optically, and/or mechanically) to one or more components internal to the implantable housing. The implantable lead can be inserted (e.g., tunneled) through tissue of the patient, such that its one or more functional elements are positioned proximate tissue to be treated and/or positioned at an area in which data is to be recorded.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g., when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set and/or modify one or more treatment and/or data recording settings of the medical apparatus of the present inventive concepts. In some embodiments, the external programmer can be configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue", or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy") delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a medical apparatus for treating and/or diagnosing a patient is illustrated, consistent with the present inventive concepts. Apparatus 10 comprises implantable system 20 and external system 50. Implantable system 20 comprises implantable device 200 shown implanted beneath the skin of patient P. In some embodiments, implantable system 20 comprises multiple implantable devices 200 (singly or collectively implantable device 200), such as is described in applicant's application International PCT Patent Serial Number PCT/US2016/051177, titled "Apparatus for Peripheral or Spinal Stimulation", filed Sep. 9, 2016, the content of which is incorporated herein in its entirety for all purposes. In some embodiments, implantable system 20 comprises at least two implantable devices, such as implantable device 200 and implantable device 200' shown in FIG. 1. Implantable device 200' can be of similar construction and arrangement to implantable device 200, and it can include components of different configuration.

External system 50 can comprise an external device 500, which includes housing 510. In some embodiments, external system 50 comprises multiple external devices 500 (singly or collectively external device 500), also as is described in applicant's application International PCT Patent Serial Number PCT/US2016/051177, titled "Apparatus for Peripheral or Spinal Stimulation", filed Sep. 9, 2016. In some embodiments, external system 50 comprises at least two external devices (e.g., at least two external devices configured to deliver power and/or data to one or more implantable devices 200), such as external device 500 and external device 500' shown in FIG. 1. External device 500' can be of similar construction and arrangement to external device 500, and it can include components of different configuration.

External system 50 can comprise external programmer 550, which can comprise a user interface, such as user interface 555. External programmer 550 can be configured to control one or more external devices 500. Alternatively or additionally, external programmer 550 can be configured to control one or more implantable devices 200 (e.g., when no external device 500 is included in apparatus 10 or otherwise no external device 500 is available to communicate with an implantable device 200.

Apparatus 10 can be configured as a patient treatment apparatus, such as a stimulation apparatus configured to stimulate tissue (e.g., stimulate nerve tissue such as tissue of the central nervous system or tissue of the peripheral nervous system, such as to neuromodulate nerve tissue), such as by having one or more implantable devices 200 deliver and/or provide energy (hereinafter "deliver energy") and/or deliver an agent (e.g., a pharmaceutical compound or other agent) to one or more tissue locations. In some embodiments, one or more implantable devices 200 deliver energy and/or an agent while receiving power and/or data from one or more external devices 500. In some embodiments, one or more implantable devices 200 deliver energy and/or an agent (e.g., continuously or intermittently) using an internal power source (e.g., a battery and/or capacitor) without receiving externally supplied power, such as for periods of at least 1 hour, at least 1 day, at least 1 month or at least 1 year. In some embodiments, one or more stimulation parameters are varied (e.g., systematically and/or randomly as described herein), during that period.

Alternatively or additionally, apparatus 10 can be configured as a patient diagnostic apparatus, such as by having one or more implantable devices 200 record a patient parameter (e.g., a patient physiologic parameter) from one or more tissue locations, such as while receiving power and/or data from one or more external devices 500. In some embodiments, during its use, one or more implantable devices 200 at least receives power from one or more external devices 500 (e.g., without also receiving data).

Alternatively or additionally, apparatus 10 can be configured as a patient information recording apparatus, such as by having one or more implantable devices 200 and/or one or more external devices 500 record patient information (e.g., patient physiologic information and/or patient environment information). In some embodiments, one or more implantable devices 200 and/or one or more external devices 500 further collect information (e.g., status information or configuration settings) of one or more of the components of apparatus 10.

In some embodiments, apparatus 10 is configured to deliver stimulation energy to tissue, such as to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, ganglia, and/or other nerve tissue. The delivered energy can comprise energy selected from the group consisting of: electrical energy; magnetic energy; electromagnetic energy; light energy such as infrared light energy. visible light energy and/or ultraviolet light energy; mechanical energy; thermal energy such as heat energy and/or cryogenic energy; sound energy such as ultrasonic sound energy (e.g., high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g., constant or otherwise controlled) electrical current and/or voltage to tissue; magnetic energy (e.g., magnetic field energy) such as by applying controlled current or voltage to a coil or other magnetic field generating element positioned proximate tissue; and/or electromagnetic energy such as by providing both current to tissue and a magnetic field to tissue. The coil or other magnetic field generating element can surround (e.g., at least partially surround) the target nerve and/or it can be incorporated as part of an anchoring system to the target tissue. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to implantable system 20, and implantable system 20 delivers stimulation energy to tissue with a stimulation signal (also referred to as a stimulation waveform), with the power signal and the stimulation signal having one or more different characteristics. The power signal can further be modulated with data (e.g., configuration or other data to be sent to one or more implantable devices 200). In these embodiments, the characteristics of the stimulation signal delivered (e.g., amplitude, frequency, duty cycle and/or pulse width), can be independent (e.g., partially or completely independent) of the characteristics of the power signal transmission (e.g., amplitude, frequency, phase, envelope, duty cycle, and/or modulation). For example, the frequency and modulation of the power signal can change without affecting the stimulation signal, or the stimulation signal can be changed (e.g., via external programmer 550), without requiring the power signal to change. In some embodiments, implantable system 20 can be configured to rectify the power signal, and produce a stimulation waveform with entirely difference characteristics (e.g., amplitude, frequency and/or duty cycle) from the rectified power signal. Implantable system 20 can comprise an oscillator and/or controller configured to produce the stimulation signal. In some embodiments, implantable system 20 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g., data and power) to implantable system 20, and implantable system 20 recovers (e.g., decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL), phase locked loop (PLL); high frequency clock; and/or crystal oscillator needed to perform the synchronization. Avoiding these components can also be correlated to reduced package size of each implantable device 200 (e.g., avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012, the content of which is incorporated herein by reference in its entirety for all purposes. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013, the content of which is incorporated herein by reference in its entirety for all purposes.

Apparatus 10 can be configured to treat a patient disease or disorder and/or it can be configured to record patient information. Apparatus 10 can be configured to treat pain, such as back pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these. In some embodiments, apparatus 10 is configured to treat a patient disease or disorder selected from the group consisting of: chronic pain; acute pain; migraine; cluster headaches; urge incontinence; overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more functional elements 260 of one or more implantable devices 200 can be implanted at one or more spinal cord locations. Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more functional elements 260 are configured to deliver energy (e.g., electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g., one or more functional elements 260 of implantable system 20) are used to record a patient parameter, such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more functional elements 260 can be positioned proximate cardiac tissue and deliver a stimulation signal as described herein (e.g., based on power and/or data received by implantable system 20 from external system 50). The stimulation signal can be used to pace, defibrillate and/or otherwise stimulate the heart. Alternatively or additionally, apparatus 10 can be configured to record cardiac activity (e.g., by recording EKG, blood oxygen, blood pressure, heart rate, ejection fraction, wedge pressure, cardiac output, lung impedance and/or other properties or functions of the cardiovascular system), such as to determine an onset of cardiac activity dysfunction or other undesired cardiac state. In some embodiments, apparatus 10 is configured to both record cardiac or other information and deliver a stimulation signal to cardiac tissue (e.g., stimulation varied or otherwise based on the recorded information). For example, apparatus 10 can be configured such that external system 50 transmits power and/or data to implantable system 20. Implantable system 20 monitors cardiac activity, and upon detection of an undesired cardiovascular state, implantable system 20 delivers a pacing and/or defibrillation signal to the tissue that is adjacent to one or more functional elements 260 configured to deliver a cardiac stimulation signal.

Apparatus 10 can be configured to perform a diagnostic procedure including measuring one or more patient parameters (e.g., patient physiologic or other patient parameters), such as are described in detail herebelow. In some embodiments, apparatus 10 is configured to measure a physiologic parameter that can be sensed from one or more sensor-based functional elements 260 positioned in subcutaneous tissue. In these embodiments, external system 50 can comprise an external device 500 configured for placement proximate an implantable device 200 implanted in a position to record data from subcutaneous tissue (e.g., blood glucose data). The external device 500 can comprise a wrist band, a wrist watch or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's ankle, knee or thigh. In some embodiments, external device 500 comprises a band or other attachment device for positioning about the thorax, neck, groin or head. Power and/or data can be sent to the implantable device 200 from the external device 500, and data (e.g., blood glucose data) can be sent to external device 500 (or another component of external system 50) by implantable device 200, such as using a communication configuration described in detail herebelow. In some embodiments, external device 500 comprises a functional element 560 configured to deliver an agent (e.g., insulin or glucose delivered by a needle-based functional element 560), based on the information received from implantable device 200. Alternatively, or additionally, implantable device 200 comprises a functional element 260 configured to deliver an agent (e.g., insulin or glucose delivered by a needle-based functional element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

External system 50 can be configured to transmit power and/or data (e.g., implantable system 20 configuration data) to one or more implantable devices 200 of implantable system 20. Configuration data provided by external system 50 (e.g., via one or more antennas 540 of one or more external devices 500) can include when to initiate stimulation delivery (e.g., energy delivery), when to stop stimulation delivery, and/or data related to the value or change to a value of one or more stimulation variables as described hereabove. The configuration data can include a stimulation parameter such as an agent (e.g., a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

External system 50 can comprise one or more external devices 500. External system 50 can comprise one or more antennas 540, such as when a single external device 500 comprises one or more antennas 540 or when multiple external devices 500 each comprise one or more antennas 540. In some embodiments, antenna 540 comprises an antenna assembly, such as such as a shielded or other antenna assembly, such as any antenna assembly 1040 described herein. The one or more antennas 540 can transmit power and/or data to one or more antennas 240 of implantable system 20, such as when a single implantable device 200 comprises one or more antennas 240 or when multiple implantable devices 200 each comprise one or more antennas 240. In some embodiments, one or more antennas 540 define a radiation footprint (e.g., a footprint defining a volume, such as a volume of tissue, in which electromagnetic transmissions radiated by antennas 540 can be properly received by antennas 240), such as is described in applicant's International PCT Patent Application Serial Number PCT/US2016/016888, titled "Medical Apparatus including an Implantable System and an External System", filed Feb. 5, 2016; the content of which is incorporated herein by reference in its entirety for all purposes.

External system 50 transmits power and/or data with a transmission signal comprising at least one wavelength, $\lambda$. External system 50 and/or implantable system 20 can be configured such that the distance between an external antenna 540 transmitting the power and/or data and one or more implantable antennas 240 receiving the power and/or data transmission signal is equal to between $0.1\lambda$, and $10.0\lambda$, such as between $0.2\lambda$, and $2.0\lambda$. In some embodiments, one or more transmission signals are delivered at a frequency range between 10 MHz and 100 MHz, such as approximately 40.68 MHz. In some embodiments, one or more transmission signals are delivered at a power level between 10 mW and 4 W, such as a power level between 10 mW and 400 mW. In some embodiments, one or more transmission signals are delivered at a frequency range between 0.1 GHz and 10.6 GHz, such as between 0.1 GHz and 3.0 GHz, between 0.4 GHz and 1.5 GHz, or between 0.902 GHz and 0.928 GHz, or in a frequency range proximate to 866 MHz, or approximately between 863 MHz and 870 MHz.

In addition to transmitting power and/or data to implantable system 20, external system 50 can be further configured to provide information (e.g., patient information and/or apparatus 10 performance information) to one or more other devices, such as tool 60 shown in FIG. 1 and described in detail herebelow.

One or more external devices 500 (singly or collectively external device 500) can be configured to transmit power and/or data (e.g., implantable system 20 configuration data) to one or more implantable devices 200. In some embodiments, one or more external devices 500 are configured to transmit both power and data (e.g., simultaneously and/or sequentially) to one or more implantable devices 200. In some embodiments, one or more external devices 500 are further configured to receive data from one or more implantable devices 200 (e.g., via data transmitted by one or more antennas 240 of one or more implantable devices 200). Each external device 500 can comprise housing 510, power supply 570, a transmitter 530, and/or one or more antennas 540, each described in detail herebelow. Each external device 500 can further comprise one or more functional elements 560, such as a functional element comprising a sensor, electrode, energy delivery element, a magnetic-field generating transducer, and/or any transducer, also described in detail herebelow. In some embodiments, a functional element 560 comprises one or more sensors configured to monitor performance of external device 500 (e.g., to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530 and/or power supply 570 shown in FIG. 1. In some embodiments, a single external device 500 comprises multiple discrete (i.e., separate) housings 510, two or more of which can transfer data or other signals via a wired or wireless connection. In some embodiments, a housing 510 further surrounds an external programmer 550 and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g., shielded to prevent transmission of electromagnetic waves), and an unshielded portion, such as an unshielded portion surrounding antenna 540.

Housing 510 can comprise an adhesive element, such as an adhesive element configured to temporarily attach an external device 500 to the patient's skin. Housing 510 can be constructed and arranged to engage (e.g., fit in the pocket of) a patient attachment device, such as patient attachment device 70 described herebelow.

One or more antennas 540 (singly or collectively antenna 540) can each comprise one or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. One or more antennas 540 can be positioned in a housing 510 that is otherwise void of other components (e.g., void of power supply 570 and transmitter 530), such as when an antenna 540 is positioned within a first housing 510 and communicates with components positioned in a second housing 510.

In some embodiments, a spacing element, spacer 591 is positioned between antenna 540 and the patient's skin, such as a spacer comprising a thickened portion of housing 510 or a discrete spacer 591 placed on a side of housing 510 (as shown) or on a side of antenna 540. Spacer 591 can comprise one or more materials that match the impedance of antenna 540 to the impedance of the patient's tissue. Spacer 591 can comprise a thickness of between 0.1 cm to 3 cm, such as a thickness between 0.2 cm and 1.5 cm. Spacer 591 can comprise materials which isolate heat (e.g., a spacer 591 comprising thermally insulating material). Alternatively, or additionally, housing 510 can comprise a heat insulating and/or dissipating material. Spacer 591 can comprise a soft or otherwise compressible material (e.g., foam) for patient comfort. Spacer 591 can be inflatable, such as to control the separation distance of an external antenna 540 from the patient's skin. An inflatable spacer 591 can be compartmentalized into several sections with independently controlled air pressure or volume to adjust the separation distance of an external antenna 540 and the patient's skin and/or its angle (e.g., tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; a loop antenna (e.g., a concentric loop antenna); antenna loaded with reactive elements; dipole antenna; quadrupole antenna; multipole antenna; polarizable antenna; selectable conductors that form an antenna; and combinations of one or more of these.

Antenna 540 can comprise a major axis between 1 cm and 10 cm, such as a major axis between 2 cm and 5 cm. Antenna 540 can be further configured to receive a signal, such as when an antenna 240 is configured to transmit data to an external device 500. Antenna 540 can be positioned on (e.g., fabricated onto) a substrate, such as a flexible printed circuit board or other printed circuit board (e.g., a single or multiple layer printed circuit board comprising electrical traces connecting components).

A single external antenna 540 can be configured to transmit power and/or data to multiple implantable devices 200 (e.g., each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g., within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 can be optimized for a different design parameter than the second antenna 540, and each antenna 540 can be activated independently or simultaneously to realize both benefits. In some embodiments, the first antenna 540 can be similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 can transmit power and/or data to the one or more antennas 240, simultaneously or sequentially. In sequential power and/or data transfers, a first external device 500 comprising a first one or more antennas 540 can be replaced (e.g., swapped) with a second external device 500 comprising a second one or more antennas 540. Alternatively or additionally, sequential power and/or data transfer can be initiated by one or more of the following conditions: when the first external antenna 540 moves (e.g., moves relative to the implanted antenna 240); when a second external device 500 comprising the second antenna 540 is turned on or otherwise activated; when the second antenna 540 provides improved power and/or data transfer to the antenna 240 than is provided by the first antenna 540; and/or when power received from the first antenna 540 decreases (e.g., decreases below a threshold). In some embodiments, an antenna 240 receives power from a first antenna 540 and a second antenna 540, but only receives data from the first antenna 540. In some embodiments, a first antenna (e.g., an antenna 240 or an antenna 540) is driven with a different carrier signal than a second antenna (e.g., an antenna 240 or an antenna 540). The two carrier signals can comprise differences in amplitudes and/or relative phases as compared to each other. Each carrier signal can include a data transmission (e.g., data to be transmitted to an implantable device 200 from an external device 500 or to an external device 500 from an implantable device 200).

One or more transmitters 530 (singly or collectively external transmitter 530) can each comprise one or more external transmitters that drive one or more antennas 540 (e.g., one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. In some embodiments, one or more transmission signals are delivered at a frequency range between 10 MHz and 100 MHz, such as approximately 40.68 MHz. In some embodiments, transmitter 530 comprises a transmitter that operates in a frequency range between 0.1 GHz and 10.6 GHz, such as a transmitter that operates in a frequency range between 0.1 GHz and 3.0 GHz, between 0.4 GHz and 1.5 GHz, between approximately 0.902 GHz and 0.928 GHz, or in a frequency range proximate to 866 MHz, or approximately between 863 MHz and 870 MHz. Transmitter 530 can comprise a transmitter that produces a transmission signal with a power level between 10 mW and 4 W, such as a power level between 10 mW and 400 mW. Transmitter 530 can comprise a transmitter that produces a transmission signal with a power level between 0.1 W and 4.0 W, such as a transmission signal with a power level between 0.1 W and 2.0 W or between 0.2 W and 1.0 W.

As described herein, one or more external devices 500 can be configured to transmit data (e.g., configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to adjust the level of power transmitted to one or more implantable devices 200, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g., when one or more implantable devices 200 are further configured to transmit data to external system 50); set a power transfer based on charge information and/or discharge information related to an implantable device 200 (e.g., charge rate and/or discharge rate of an implantable energy storage assembly 270); and combinations of one or more of these. In some embodiments, implantable system 20 comprises a first receiver 230 (e.g., of a first implantable device 200) and a second receiver 230 (e.g., of a second implantable device 200'). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 530 (and/or another component of external system 50) is further configured as a receiver, such as to receive data from implantable system 20. For example, a transmitter 530 can be configured to receive data via one or more antennas 240 of one or more implantable devices 200. Data received can include patient information (e.g., patient physiologic information, patient environment information or other patient information) and/or information related to an implantable system 20 parameter (e.g., an implantable device 200 stimulation parameter and/or other configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as an external programmer 550, cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 560 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g., via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g., serially replaced) by the second battery. In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source.

Each external programmer 550 (singly or collectively external programmer 550 or programmer 550) comprises a programming device configured to control one or more components of apparatus 10. Programmer 550 can comprise a user interface 555. Programmer 550 can send and/or receive commands to and/or from one or more external devices 500 via a wireless or wired connection (wired connection not shown but such as one or more insulated conductive wires). In some embodiments, one or more external devices 500 comprise programmer 550, such as when user interface 555 is integrated into housing 510 of external device 500. In some embodiments, apparatus 10 comprises multiple programmers 550.

External programmer 550 can be configured to adjust one or more parameters of apparatus 10, such as a stimulation parameter (e.g., a stimulation waveform parameter as described herein); a sensing parameter; a therapy parameter; a data recording parameter (e.g., a patient data recording parameter and/or an implantable device 200 data recording parameter); power transfer; data rate; activity of one or more external transmitters 530; activity of one or more external antennas 540; a functional element 260 parameter; a functional element 560 parameter; and combinations of one or more of these, such as is described hereabove. Programmer 550 can be further configured to provide information, such as patient physiologic information recorded by one or more implantable devices 200, or apparatus 10 information, such as performance and/or configuration information (singly or collectively "status information") of one or more external devices 500 and/or implantable devices 200. In some embodiments, the programmer 550 uses information recorded by one or more implantable devices 200, apparatus 10 information, and/or information from external devices 500 to adapt configuration parameters of one or more components of apparatus 10.

In some embodiments, external programmer 550 can be configured to confirm that an adequate power transmission and/or an adequate data transmission has occurred between one or more external devices 500 and one or more implantable devices 200. In these embodiments, programmer 550 can comprise diagnostic assembly 91 described herebelow, or otherwise be configured to detect one or more of: power transmission to the implantable system 20 (e.g., to detect power transmission to implantable system 20 below a threshold); power transmission to the implantable system 20 trending in an undesired direction; improper and/or inadequate data transfer to the implantable system 20; and combinations of one or more of these. In some embodiments, the programmer 550 monitors power transfer in real time and adjusts power transmission accordingly to optimize the rectifier 232 efficiency of one or more implantable devices 200. In some embodiments, apparatus 10 can be configured to adjust (e.g., in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These adjustments can include adjustment to one or more of: power transmission amplitude, duty cycle, frequency, phase, and periodicity.

In some embodiments, programmer 550 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 550 can be configured to monitor a standing wave pattern at the output of the transmitter 530.

In some embodiments, external programmer 550 comprises a lookup table of stimulation signal waveform patterns, such as to allow a clinician, patient and/or other operator of apparatus 10 to select a predetermined stimulation pattern. In some embodiments, programmer 550 comprises a set of adjustable stimulation signal parameters configured to be varied to allow an operator to construct customized waveforms, such as to vary one or more stimulation parameters described hereabove. In some embodiments, the programmer 550 is configured to allow an operator to create a customized waveform by specifying an amplitude of one or more discrete pulses or steps of a stimulation signal.

In some embodiments, external programmer 550 comprises a transmitter configured to transmit data to tool 60 or another device such as a cell phone; computer; tablet; computer network such as the internet or a LAN; and combinations of one or more of these. In these embodiments, programmer 550 can comprise a wireless transmitter; a Bluetooth transmitter; a cellular transmitter; and combinations of one or more of these. In some embodiments, external programmer 550 comprises a receiver configured to receive data, or a transceiver configured to both transmit and receive data.

User interface 555 of external programmer 550 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 560, such as functional elements 560a and/or 560b (singly or collectively functional element 560), shown positioned in programmer 550 and in external device 500, respectively. Each functional element 560 can comprise a sensor, an electrode, an energy delivery element, an agent delivery element, a magnetic field generating transducer, and/or any transducer. In some embodiments, one or more functional elements 560 comprise a transducer selected from the group consisting of: light; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, functional element 560 comprises a needle, a catheter (e.g., a distal portion of a catheter), an iontophoretic element or a porous membrane, such as an agent delivery element configured to deliver one or more agents contained (e.g., one or more agents in a reservoir, such as reservoir 525 described herebelow) within an external device 500 and delivered into the patient (e.g., into subcutaneous tissue, into muscle tissue and/or into a blood vessel such as a vein).

In some embodiments, the functional element 560 can comprise an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more functional elements 260.

In some embodiments, one or more functional elements 560 comprise a sensor, such as a sensor configured to record data related to a patient parameter (e.g., a patient physiologic parameter), an external system 50 parameter and/or an implantable system 20 parameter. In some embodiments, operation of one or more implantable devices 200 (e.g., stimulation energy delivered by one or more implantable devices 200) is configured to be delivered based on the data recorded by one or more sensor-based functional elements 560, such as in a closed-loop energy delivery mode.

Functional element 560 can comprise one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

Functional element 560 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity; electrical activity produced by skeletal muscles (e.g., as measured using electromyography, EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 560 can comprise one or more sensors configured to record data representing a parameter of external system 50 or any component of apparatus 10. Functional element 560 can comprise one or more sensors selected from the group consisting of: an energy sensor; a voltage sensor; a current sensor; a temperature sensor (e.g., a temperature of one or more components of external device 500 or programmer 550); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g., via controller 250 described herebelow) the data recorded by functional element 560 to assess one or more of: power transfer; link gain; power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 560 are positioned on a housing 510. A functional element 560 can comprise a body conduction sensor, such as a body conduction sensor configured to record and/or receive data via skin conduction. A functional element 560 can be configured to record data associated with stimulation delivered by one or more implantable devices 200 (e.g., record data associated with stimulation energy delivered by one or more functional elements 260), such as to provide closed loop or semi-closed loop stimulation. A functional element 560 can be configured to record temperature, such as when apparatus 10 is configured to deactivate or otherwise modify the performance of an external device 500 when the recorded temperature (e.g., patient temperature and/or external device 500 temperature) exceeds a threshold.

In some embodiments, external programmer 550 and/or an external device 500 can comprise a temperature sensor, such as functional elements 560a and 560b shown, respectively. The temperature-based functional element 560 can be positioned proximate a portion of programmer 550, housing 510 and/or one or more antennas 540 (e.g., to measure the temperature of one or more portions of a programmer 550 and/or external device 500). In these embodiments, the temperature data recorded by the functional element 560 is used to adjust one or more of: matching network; stimulation level (e.g., stimulation energy delivered by one or more implantable devices 200); power transmission level (e.g., level of power transmitted between one or more external devices 500 and one or more implantable devices 200); and combinations of one or more of these. In some embodiments, the temperature sensor-based functional element 560 is a part of a safety mechanism that deactivates programmer 550 and/or an external device 500 if the recorded temperature exceeds a threshold. Alternatively or additionally, a temperature sensor-based functional element 560 can be configured to measure temperature of the patient, such as when placed on housing 510, such as to adjust energy and/or agent delivery performed by implantable device 200 based on the recorded patient temperature.

Implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200. Each implantable device 200 can be configured to treat a patient (e.g., treat pain of the patient) and/or record patient information, such as by delivering energy and/or an agent to tissue and/or by recording one or more physiologic parameters of tissue.

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g., during and/or after implantation) via an imaging device such as a CT, X-ray, fluoroscope, ultrasound imager and/or MRI.

In some embodiments, implantable system 20 comprises multiple implantable devices 200 (e.g., implantable device 200 and implantable device 200' shown in FIG. 1) and implantable system 20 comprises a "multi-point ready" system, in which the operation (e.g., energy delivery, agent deliver, data recording and/or other function) of the multiple implantable devices 200 is performed simultaneously, asynchronously, and/or sequentially. The implantable devices 200 can be part of a network including one or more external devices 500 (e.g., external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single or multiple external devices 500, which can further be synchronized to a single clock. Each implantable device 200 of implantable system 20 can receive a power signal and/or a data signal from one or more external devices 500. In some embodiments of the multi-point ready implantable system 20, each implantable device 200 comprises a unique ID, such that each implantable device 200 can be individually addressed (e.g., receive unique signals from external system 50). In some embodiments, external system 50 transmits high-bandwidth signals to implantable system 20, such that time-domain multiple access communication can be performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g., two components comprising or positioned in different housings), can be attached to each other by a connecting filament as defined hereabove. In some embodiments, a connecting filament comprises a user-attachable (e.g., clinician-attachable) connector on at least one end. The filament connector is configured to operably attach to a mating connector on a component (e.g., a housing 210) of an implantable device 200.

Each implantable device 200 is configured to receive power and/or data (e.g., implantable system 20 configuration data) from one or more external devices 500. In some embodiments, one or more implantable devices 200 are configured to receive both power and data (e.g., simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more functional elements 260, configured to stimulate, deliver energy to, deliver an agent to, record information from and/or otherwise interface with the patient. Alternatively or additionally, the one or more functional elements 260 can be configured to record patient information. Each implantable device 200 can comprise housing 210, receiver 230, controller 250, energy storage assembly 270 and/or one or more antennas 240, each described in detail herein. In some embodiments, antenna 240 comprises an antenna assembly, such as such as a shielded or other antenna assembly, such as any antenna assembly 1040 described herein. Each functional element 260 can comprise a sensor and/or any transducer, as described in detail herein. One or more functional elements 260 can be positioned on a lead 265 (e.g., a flexible filament including wires or other conductors that connect each functional element to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can further comprise one or more anchor elements 221, as described in detail herebelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g., patient physiologic information recorded by one or more functional elements 260 configured as a physiologic sensor), or implantable device 200 information (e.g., data recorded by one or more functional elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more functional elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g., a flexible or foldable printed circuit board).

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm. Housing 210 can comprise a wall thickness between 0.2 mm and 1.0 mm, such as a wall thickness between 0.2 mm and 0.5 mm, such as a wall thickness of approximately 0.3 mm. Housing 210 can comprise a displacement volume less than or equal to 2000 mm$^3$, such as less than or equal to 600 mm$^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g., shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's International PCT Patent Application Serial Number PCT/US2016/016888, titled "Medical Apparatus including an Implantable System and an External System", filed Feb. 5, 2016; the content of which is incorporated herein by reference in its entirety for all purposes.

In some embodiments, one or more inner or outer surfaces (or portions of surfaces) of housing 210 includes an insulating and/or shielding layer (e.g., a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating 219, while other portions are transmissive to electromagnetic signals such as radiofrequency signals.

In some embodiments, housing 210 comprises an array of feedthroughs, not shown. In some embodiments, housing 210 is surrounded by a covering, such as a flexible and/or non-conductive covering, such as a covering made of an elastomer.

In some embodiments, one or more implantable devices 200 comprises one or more anchor elements configured to secure one or more portions of implantable device 200 to tissue, such as anchor element 221 shown positioned on housing 210. Anchor element 221 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g., two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g., a substrate comprising rigid portions and hinged portions). In some embodiments, the substrate can be folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 can comprise an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g., positioned on two relatively orthogonal planes). In some embodiments, a first antenna (e.g., an electrical dipole antenna) is positioned outside of housing 210, while a second antenna (e.g., a loop antenna) and a third antenna (e.g., a loop antenna) are each positioned on, in and/or within housing 210. In some embodiments, implantable device 200 can comprise one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's U.S. patent application Ser. No. 14/975,358, titled "Method and Apparatus for Minimally Invasive Implantable Modulators", filed Dec. 18, 2015, the content of which is incorporated herein by reference in its entirety for all purposes.

One or more antennas 240 can be positioned inside of housing 210. Alternatively or additionally, one or antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g., rechargeable batteries) and/or capacitors (e.g., a supercapacitor). Energy storage assembly 270 can be configured to provide power to one or more of: one or more functional elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 μF and 10 F, such as a capacitance between 1 μF and 1.0 mF, or between 1 μF and 10 μF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g., maintain delivery of stimulation energy and/or delivery of an agent) without the use (e.g., sufficient proximity) of an associated external device 500. A capacitor or other energy storage element (e.g., a battery) can be chosen to provide sufficient energy to maintain operation for at least 30 seconds, at least 2 minutes, at least 5 minutes, at least 30 minutes, and up to several hours or more (e.g., during showering, swimming or other physical activity). In some embodiments, energy storage assembly 270 is configured to provide continuous and/or intermittent stimulation energy for at least one charge-balanced pulse (e.g., for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g., an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more functional elements 260 to delivery stimulation energy during subsequent (intended or unintended) unavailability of one or more external devices 500 (e.g., an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

One or more controllers 250 (singly or collectively controller 250) can be configured to control one or more functional elements 260, such as a functional element 260 comprising a stimulation-based transducer (e.g., an electrode or other energy delivery element) and/or a sensor (e.g., a physiologic sensor and/or a sensor configured to monitor an implantable device 200 parameter). In some embodiments, controller 250 is configured to transmit a stimulation signal (e.g., transmit stimulation energy configured in one or more stimulation waveforms) to one or more functional elements 260 (e.g., one or more functional elements 260 comprising an electrode and/or other energy delivery element), independent of the power signal received by one or more antennas 240 (e.g., independent of power transmitted by external system 50), such as by using energy stored in energy storage assembly 270. In these embodiments, the power signal and/or the RF path for the power signal can be adjusted to optimize power efficiency (e.g., by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g., by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g., unaffected). In some configurations, the stimulation signal being delivered by one or more implantable devices 200 can be insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; functional element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these.

In some embodiments, one or more functional elements 260 comprise a stimulation element configured to deliver energy (e.g., one or more electrodes configured to deliver monopolar or bipolar electrical energy) to tissue, and controller 250 is configured to control the energy delivery, such as to control one or more stimulation parameters as described herein. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described herebelow. In some embodiments, stimulation (e.g., stimulation comprising high frequency and/or low frequency signal components) is varied randomly to eliminate or at least reduce synchrony of neuronal firing with the stimulation signal (e.g., to reduce paresthesia or other patient discomfort). In some embodiments, one or more functional elements 260 comprise a stimulation element configured to stimulate a target (e.g., nerve tissue such as spinal nerve tissue and/or peripheral nerve tissue). The amount of stimulation delivered to the target can be controlled by varying a parameter selected from the group consisting of: functional element 260 size and/or configuration (e.g., electrode size and/or configuration); functional element 260 shape (e.g., electrode shape, magnetic field generating transducer shape or agent delivering element shape); shape of a generated electric field; shape of a generated magnetic field; stimulation signal parameters; and combinations of one or more of these.

In some embodiments, one or more functional elements 260 comprise an element configured to deliver electrical energy to tissue (e.g., one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.1 mA to 15 mA (such as between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g., greater than 10 μF), in order to pass the stimulation waveform with minimal filtering. In some embodiments, apparatus 10 can be configured to perform active charge balancing. In some embodiments, an implantable device 200 can comprise a precise resistor in series with a stimulation electrode-based functional element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g., a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g., pulses delivered within a train or a burst). Implantable device 200 can comprise a precise series resistance comprising an on-chip trimmed resistor or an off chip resistor. In some embodiments, implantable device 200 comprises a bank of trimmed resistors that are used to control the net series resistance, such as to adjust resistance based on stimulation amplitude requirements (e.g., to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more functional elements 260 configured as a stimulation element (e.g., such that one or more functional elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g., symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g., an operator customized waveform), such as by adjusting amplitude at specified time steps (e.g., for one or more pulses). In some embodiments, controller 250 is configured to generate a waveform including one or more random parameters (e.g., random timing of pulses or random changes in frequency, rate of change or amplitude).

In some embodiments, controller 250 is configured to provide a stimulation signal comprising waveforms and/or pulses repeated at a frequency (e.g., includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g., signal) between 1 kHz and 20 kHz. In some embodiments, controller 250 is configured to produce a stimulation signal comprising a mix and/or modulation of low frequency and high frequency signals, which can be of any of the waveform types, shapes and other configurations as described herein. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, functional element 260 drivers (e.g., electrode drivers) of controller 250, and/or other components of implantable device 200. The clamping circuit can improve pulse shape by offering additional control and/or configuration of rise and fall times in the shape of the waveform (e.g., to create rapid rise or fall times). In some embodiments, the clamping circuit can be configured to limit the rise and/or fall time to be less than or equal to one-tenth (10%) of the pulse width of an applied stimulation pulse (e.g., less than or equal to 1 µs rise and/or fall time for a 10 µs stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232 and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g., to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable device 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that can be used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or be further boosted by a DC-DC converter or boost converter. In some embodiments, rectifier 232 can comprise diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more functional elements 260. Lead 265 can comprise one or more functional elements 260 configured as a stimulation element (e.g., an electrode configured to deliver electrical energy in monopolar or bipolar mode or an agent delivery element such as an output port fluidly connected to a reservoir within housing 210). Alternatively or additionally, lead 265 can comprise one or more functional elements 260 configured as a physiologic sensor (e.g., an electrode configured to record electrical activity of tissue or other physiologic sensor as described herein). Alternatively or additionally, lead 265 can comprise one or more functional elements 260 configured to transmit signals through tissue to external system 50, such as through body conduction.

In some embodiments, lead 265 comprises a removable stylet configured to aid in the implantation of lead 265, such as is described in applicant's International PCT Patent Application Serial Number PCT/US2016/016888, titled "Medical Apparatus including an Implantable System and an External System", filed Feb. 5, 2016; the content of which is incorporated herein by reference in its entirety for all purposes. In some embodiments, implantable system 20 comprises more than one lead 265, comprising one or more functional elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm. In some embodiments, lead 265 comprises a length between 3 cm and 60 cm, such as a length between 6 cm and 30 cm. One or more leads 265 can include between 2-64 functional elements 260, such as when a lead 265 comprises between 2 and 64 electrodes, such as between 4 and 32 electrodes. In some embodiments, lead 265 can comprise a paddle lead. In some embodiments, lead 265 comprises a single or multi-lumen catheter, such as when an attached implantable device 200 is configured as an agent delivery apparatus as described herein (e.g., a functional element 260 configured as a catheter comprises at least a portion of lead 265).

One or more functional elements 260 (singly or collectively functional element 260) can comprise one or more sensors, transducers and/or other functional elements. In some embodiments, functional elements 260 comprise at least one sensor and/or at least one transducer (e.g., a single functional element 260 or multiple functional elements 260). In some embodiments, functional element 260 comprises a functional element configured to provide a therapy, such as one or more functional elements 260 configured to deliver an agent to tissue (e.g., a needle or catheter), to deliver energy to tissue and/or to otherwise affect tissue. In some embodiments, functional element 260 comprises one or more functional elements 260 configured to record patient information, such as when functional element 260 comprises one or more sensors configured to measure a patient physiologic parameter, as described herein. In some embodiments, functional element 260 comprises one or more sensors configured to record an implantable device 200 parameter, also as described herein.

One or more functional elements 260 can be positioned on lead 265 as shown in FIG. 1. Alternatively or additionally, one or more functional elements 260 can be positioned on housing 210.

Functional element 260 can comprise one or more functional elements positioned at one or more internal body locations. Functional element 260 can comprise one or more functional elements positioned to interface with (e.g., deliver energy to and/or record a physiologic parameter from) spinal cord tissue, spinal canal tissue, epidural space tissue, spinal root tissue (dorsal or ventral), dorsal root ganglion, nerve tissue (e.g., peripheral nerve tissue, spinal nerve tissue or cranial nerve tissue), brain tissue, ganglia (e.g., sympathetic or parasympathetic) and/or a plexus. In some embodiments, functional element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the functional element 260 is positioned proximate to and/or within. In some embodiments, apparatus 10, implantable device 200 and/or functional element 260 are configured to stimulate spinal nerves, peripheral nerves and/or other tissue as described in applicant's application International PCT Patent Serial Number PCT/US2016/051177, titled "Apparatus for Peripheral or Spinal Stimulation", filed Sep. 9, 2016.

In some embodiments, functional element 260 comprises one or more sensors configured to record data representing a physiologic parameter of the patient. Functional element 260 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 and functional element 260 can be configured to record a patient parameter (e.g., patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, functional element 260 comprises one or more sensors configured to record data representing a parameter of implantable device 200. In these embodiments, functional element 260 can comprise one or more sensors selected from the group consisting of: an energy sensor; a voltage sensor; a current sensor; a temperature sensor (e.g., a temperature of one or more components of implantable device 200); a contamination detector (e.g., to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g., via implantable controller 250, programmer 550 and/or diagnostic assembly 91 described herebelow) the data recorded by functional element 260 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A functional element 260 can be configured to record temperature, such as when apparatus 10 is configured to deactivate or otherwise modify the performance of an implantable device 500 when the recorded temperature exceeds a threshold.

In some embodiments, one or more functional elements 260 comprise a transducer configured to deliver energy to tissue, such as to treat pain and/or to otherwise stimulate or affect tissue. In some embodiments, functional element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g., delivering mechanical energy to tissue); a tissue manipulating element; a heat generating element; a cooling (e.g., cryogenic or otherwise heat extracting energy) element; an agent delivery element such as a pharmaceutical drug delivery element; and combinations of one or more of these.

In some embodiments, one or more functional elements 260 comprises a drug or other agent delivery element, such as a needle, port, iontophoretic element, catheter, or other agent delivering element that can be connected to a reservoir of agent positioned within housing 210 (e.g., reservoir 225 described herebelow). In some embodiments, one or more functional elements 260 comprise a drug eluting element configured to improve biocompatibility of implantable system 20.

In some embodiments, one or more functional elements 260 comprise one or more electrodes configured to deliver energy to tissue and/or to sense a patient parameter (e.g., electrical activity of tissue or other patient physiologic parameter). In these embodiments, one or more functional elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 and functional element 260 are configured to both record one or more patient parameters, and also to perform a medical therapy (e.g., stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more functional elements 260 comprise an agent delivery element, such as a fluid delivery element (e.g., a catheter, a porous membrane, an iontophoretic element or a needle) in fluid communication with a reservoir of the agent positioned within housing 210, such as reservoir 225 described herebelow.

In some embodiments, apparatus 10 comprises tool 60. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g., patient physiologic information) recorded by implantable system 20; patient environment information recorded by implantable system 20; and combinations of one or more of these. Tool 60 can be configured to receive data from wired or wireless (e.g., Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

In some embodiments, tool 60 comprises an implantation tool, such as an introducer or other implantation tool constructed and arranged to aid in the implantation of housing 210, implantable antenna 240, lead 265 and/or one or more functional elements 260.

In some embodiments, lead 265 comprises a paddle lead or other stimulating lead and tool 60 comprises an introducer (e.g., a needle or an extended-width introducer) configured to deliver at least a distal portion of lead 265 into an epidural space of a patient. Tool 60 can comprise an introducer comprising a Tuohy needle, such as a Tuohy needle of 12 gauge or smaller. Tool 60 can comprise a handle for manipulating lead 265. Tool 60 can be configured to place lead 265 at an entry point above the lumbar spinal column (e.g., between L1 and L2 vertebrae). Tool 60 can include extension tubing used to insert lead 265. Tool 60 can further comprise a tool configured to anchor lead 265, such as when tool 60 comprises sutures, clips, other anchoring elements and/or an anchor securing tool (e.g., a needle or a stapling device), such as to secure lead 265 in subcutaneous tissue. Lead 265 and/or tool 60 can comprise extension tubing used to place lead 265, such as extension tubing that remains in place after removal of an introducer of tool 60. Tool 60 can be configured to place lead 265 against the dura of the spinal cord of the patient.

In some embodiments, tool 60 and/or lead 265 are constructed and arranged to implant lead 265 to stimulate one or more multifidus (MF) muscle fascicles, such as at least three sets of multifidus muscle fascicles. Lead 265 can be secured to a vertebra (e.g., on the transverse process, lamina or vertebral body). Lead 265 can placed via tool 60 such that one or more functional elements 260 (e.g., electrodes) are positioned within the multifidus muscle structures. One or more functional elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Functional elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, functional elements 260 are positioned to cause transvascular stimulation (e.g., transvascular stimulation from arteries and/or veins in a leg or arm). In some embodiments, functional elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, functional elements 260 are configured to deliver stimulation energy to contract the multifidus muscle. In some embodiments, functional elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g., an RF transmitter), magnetic coupling, capacitive coupling and/or other wireless transmission means, Apparatus 10 can include one or more devices, such as patient attachment device 70 shown in FIG. 1, that is used to attach one or more portions of external system 50 to a location on or proximate the patient. In some embodiments, patient attachment device 70 is constructed and arranged as described in applicant's International PCT Patent Application Serial Number PCT/US2015/036821, titled "Method and Apparatus for Neuromodulation Treatments of Pain and Other Conditions", filed Jun. 19, 2015, the content of which is incorporated herein by reference in its entirety for all purposes.

Patient attachment device 70 can comprise one or more elements configured to attach one or more external devices 500 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive, adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g., at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 550; and combinations of one or more of these. In some embodiments, patient attachment device 70 comprises multiple pockets, such as to allow repositioning of an external antenna 540, programmer 550, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that can accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

Apparatus 10 can comprise a device configured to operate (e.g., temporarily operate) one or more implantable devices 200, such as trialing interface 80 shown in FIG. 1. Trialing interface 80 can be configured to deliver power to an implantable device 200, deliver data to an implantable device 200, and/or receive data from an implantable device 200. Trialing interface 80 can be configured to interface with one or more implantable devices 200 during an implantation procedure in which one or more implantable device 200 are implanted in a patient (e.g., a sterile clinical procedure). Trialing interface 80 can be configured to be sterilized one or more times. Trialing interface 80 can comprise one or more antennas, such as an antenna similar to antenna 540 of an external device 500. Trial interface 80 can comprise a transmitter, such as a transmitter similar to transmitter 530 of external device 500, and a power supply, such as a power supply similar to power supply 570 of external device 500. In some embodiments, trialing interface is of similar construction and arrangement to the trialing interface described in applicant's International PCT Patent Application Serial Number PCT/US2015/036821, titled "Method and Apparatus for Neuromodulation Treatments of Pain and Other Conditions", filed Jun. 19, 2015, the content of which is incorporated herein by reference in its entirety for all purposes. In some embodiments, trialing interface 80 includes a housing to be positioned proximate at least a portion of implantable device 200, such as a housing that surrounds an antenna and a transmitter that is configured to operatively couple to (e.g., transmit power and/or data to) one or more antennas 240 of one or more implantable devices 200.

In some embodiments, one or more implantable devices 200 of implantable system 20 can comprise an implantable transmitter configured to transmit data, such as to transmit data (e.g., stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e., "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 91 shown in FIG. 1. In some embodiments, programmer 550 and/or implantable controller 250 comprise all or a portion of diagnostic assembly 91. Diagnostic assembly 91 can be configured to assess, monitor, determine and/or otherwise analyze patient information and/or implantable device 200 information, such as when one or more functional elements 260 and/or 560 are configured as a sensor configured to record patient information (e.g., patient physiologic information and/or patient environment information) and/or apparatus 10 information (e.g., implantable device 200 information) as described herein. Diagnostic assembly 91 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g., such as during a calibration procedure). The BER can be tracked by the implant controller 250 or programmer 550, such as to monitor and keep track of any trends in the link. This trend can be used to adjust the link and/or provide feedback to an operator of apparatus 10 (e.g., the patient), in case the link cannot be automatically adjusted to compensate for a negative trend (e.g., such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 91 can be configured to analyze a result of stimulation energy delivered by implantable device 200, such as when a functional element 260 comprises an electrode to record electrical activity of tissue (e.g., in addition to delivering electrical energy to stimulate tissue). A functional element 260 and/or 560 can comprise a sensor configured to record neural activity and/or muscular activity, and the diagnostic assembly configured to analyze the recorded sensor data. In some embodiments, diagnostic assembly 91 can be configured to analyze impedance, such as when a functional element 260 and/or 560 comprises a sensor configured to record data related to impedance, such as when implantable device 200 performs a frequency sweep, performs an impulse response and/or compares voltage and current of a stimulation waveform. In some embodiments, diagnostic assembly 91 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 91 is configured to test or otherwise assess the link between one or more implantable antennas 240 and one or more external antennas 540 (e.g., during a procedure in which one or more implantable devices 200 are implanted in a patient). In these embodiments, diagnostic assembly 91 can be configured to perform a test prior to anchoring housing 210 to tissue (e.g., prior to initial or final suturing into tissue such as the fascia layer). For example, lead 265 can be implanted at a location to stimulate target tissue (e.g., one or more nerves identified to treat pain or another patient condition). Prior to suturing housing 210 in its permanent location, diagnostic assembly 91 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 91 can comprise a handheld assembly (e.g., a sterile assembly comprising a wand or other handheld housing). Diagnostic assembly 91 can be configured to send a simple signal to one or more implantable devices 200 (e.g., a diagnostic assembly 91 with similar power and/or data transmission capabilities as an external device 500). Each implantable device 200 can respond (e.g., via data sent via an implantable antenna 240 or other transmitter) with information related to the quality of the transmission link (e.g., information about the power received by the one or more implantable devices 200). Diagnostic assembly 91 could provide a user interface (e.g., a speaker, a text screen and/or a video display) that provides quality or other information (go/no go information, digital or other discrete level information, and/or analog information). Diagnostic assembly 91 could be further configured to provide information confirming detection of one or more implantable devices 200, status of one or more implantable devices 200 (e.g., parameter level and/or fault detection status), and/or self-diagnostic status (i.e., diagnostic assembly 91 status).

Each implantable device 200 can be configured to specifically identify and/or specifically reply to diagnostic assembly 91 (e.g., in a different form than communications with an external device 500). Each implantable device 200 can be configured to provide information related to one or more of: the charge and/or discharge rate of energy storage assembly 270 (e.g., the charge and/or discharge rate of a capacitor or battery of energy storage assembly 270); or the frequency of a voltage-controlled oscillator that is driven by an unregulated voltage of power converter 233. Diagnostic assembly 91 can be configured to perform numerous performance tests (e.g., of one or more implantable devices 200 or implantation locations for one or more implantable devices 200), prior to completion of the implantation procedure (e.g., prior to closing one or more incisions).

In some embodiments, apparatus 10 is configured to provide a therapy by delivering stimulation energy to tissue, such as electrical energy delivered to tissue by one or more functional elements 260 comprising one or more electrodes. Alternatively or additionally, apparatus 10 can be configured as an agent-delivery apparatus (e.g., a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 560 and/or 260, respectively (e.g., via one or more tubes). Reservoirs 525 and/or 225 can comprise one or more chambers (e.g., independent chambers configured to separately contain incompatible drugs or otherwise prevent undesired multiple drug interactions). Reservoirs 525 and/or 225 can comprise a volume (e.g., a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g., a peristaltic mechanism, syringe pump or other fluid pump). Reservoirs 525 and/or 225 and can comprise refillable reservoirs (e.g., when reservoir 225 of an implantable device 200 comprises a valved opening such as a silicone septum or a mechanical valve, either accessible via a needle for refilling). The fluidly attached functional elements 560 and/or 260 can comprise a fluid delivery element selected from the group consisting of: a catheter; a porous membrane; an iontophoretic element; a needle; or combinations of one or more of these. Delivered and/or stored (e.g., in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g., throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g., via a catheter-based functional element 560 and/or 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e., arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 560 configured as agent delivery elements and/or sensors. The one or more implantable devices 200 can comprise one or more reservoirs 225 described hereabove and/or one or more functional elements 260 configured as agent delivery elements and/or sensors.

In some embodiments, apparatus 10 comprises an agent delivery apparatus and agent is delivered into the patient (e.g., into a blood vessel, muscle or subcutaneous tissue) by an external device 500 functional element 560 (e.g., a needle) based on signals recorded by an implantable device 200 functional element 260 (e.g., a sensor). Alternatively or additionally, agent can be delivered into the patient (e.g., into a blood vessel, muscle or subcutaneous tissue) by an implantable device 500 functional element 260 (e.g., a needle, catheter, porous membrane or iontophoretic delivery element). The amount of agent delivered by functional element 260 can be based on signals recorded by an implantable device 200 functional element 260 (e.g., a sensor) and/or an external device 500 functional element 560 (e.g., a sensor). External device 500 can provide power to one or more implantable devices 200 and/or it can send data (e.g., sensor data from a functional element 560) to implantable device 500, such as to control agent delivery by implantable device 500.

Apparatus 10 can be configured to prevent an electromagnetic field (e.g., an electromagnetic field produced by one or more devices not included in apparatus 10 and/or other present in the patient environment) from adversely affecting and/or otherwise affecting the patient treatment and/or patient information recording (e.g., patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g., stimulation). In some embodiments, external system 50 and/or implantable system 20 can incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g., and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its functional elements 260 (e.g., electrodes) can be configured to provide localized (e.g., targeted) magnetic and/or electrical stimulation. Combined electrical field stimulation and magnetic field stimulation can be applied by using superposition, and can reduce the overall energy requirement. In some embodiments, implantable apparatus 10 comprises one or more functional elements 260 comprising a magnetic field generating transducer (e.g., microcoils or cuff electrodes positioned to partially surround or otherwise be proximate to one or more target nerves). Functional elements 260 comprising microcoils can be aligned with nerves to minimize affecting non-targeted tissue (e.g., to avoid one or more undesired effects to non-target tissue surrounding or otherwise proximate the target tissue). In some embodiments, the target tissue comprises DRG tissue, and the non-target tissue comprises ventral root tissue (e.g., when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation change between antennas and/or relative angular misalignment between antennas. In order to compensate for misaligned antennas, electrical beam steering can be included in apparatus 10. Antennas comprising a multi-feed antenna structure and/or an array of antennas can be incorporated (e.g., into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g., a substrate comprising polyamide, polyimide, liquid crystal polymer (LCP), Rogers, FR4, or a similar material). One or more antennas 540 can be connected to electronics (e.g., a transmitter, receiver or transceiver) using a flexible waveguide or cable (e.g., 50 Ohm 0.047" coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g., a piezoelectric actuator) with directional gears configured to translate one or more antennas 240 and/or 540 about one or more axes; a micro-pump with fluid reservoir (e.g., liquid or gas reservoir) configured to hydraulically and/or pneumatically translate one or more antennas 240 and/or 540 about one or more axes, such as by creating a local pressure difference. In some embodiments, a micro-pump with fluid reservoir can be used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g., a balloon) positioned between external antenna 540 and tissue. The reservoir can be inflated or deflated to control separation distance of the external antenna 540 from the patient's skin surface. In some embodiments, apparatus 10 comprises one or more algorithm positioning algorithms, beam steering functionality and/or mechanical antenna steering as described in applicant's U.S. patent application Ser. No. 14/975,358, titled "Method and Apparatus for Minimally Invasive Implantable Modulators", filed Dec. 18, 2015, or International PCT Patent Application Serial Number PCT/US2016/016888, titled "Medical Apparatus including an Implantable System and an External System", filed Feb. 5, 2016, the content of each of which is incorporated herein in its entirety for all purposes.

In some embodiments, implantable system 20 of apparatus 10 is configured to provide paresthesia-reduced (e.g., paresthesia-free) high frequency pain management and rehabilitation therapy (e.g., via delivery of a stimulation signal above 600 Hz or 1 kHz, or other stimulation signal resulting in minimal paresthesia). Apparatus 10 can be configured to provide both low frequency (e.g., <1 kHz) stimulation and high frequency stimulation, such as when providing low frequency stimulation to elicit feedback from a patient during intraoperative or other (e.g., post-implantation) stimulation configuration. For example, trialing interface 80 can be used during an intra-operative titration of stimulation configuration using low frequency stimulation (e.g., to position and/or confirm position of one or more functional elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g., via low frequency stimulation and/or high frequency stimulation) is beneficial during functional element 260 (e.g., electrode) implantation because a patient can provide feedback to the implanting clinician to ensure that the functional elements 260 are positioned close to the target neuromodulation or energy delivery site. This implantation position-optimizing procedure can advantageously reduce the required stimulation energy due to functional elements 260 being closer to target tissue, since a minimum threshold for efficacious stimulation amplitude is proportional to the proximity of functional elements 260 to target tissue (e.g., target nerves). The patient can inform the clinician of the sensation of paresthesia coverage, and the clinician can adjust functional element 260 position to optimize functional element 260 location for efficacious treatment while minimizing unintentional stimulation of non-target tissue (e.g., motor nerves or other nerves which are not causing the patient's pain). These paresthesia-inducing techniques (e.g., using low frequency stimulation and/or high frequency stimulation) can be used during or after implantation of one or more implantable devices 200.

In some embodiments, apparatus 10 is configured to deliver low frequency stimulation energy (e.g., electrical energy comprising a low frequency signal) to stimulate motor nerves, such as to improve tone and structural support (e.g., physical therapy). In these embodiments, apparatus 10 can be further configured to provide high frequency stimulation, such as to treat pain (e.g., suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g., electrical energy) to induce paresthesia, which can also be accompanied by the delivery of high frequency stimulation (e.g., to suppress and/or control pain). In some embodiments, apparatus 10 is configured to deliver low frequency stimulation (e.g., electrical energy comprising a low frequency signal) and burst stimulation, delivered simultaneously or sequentially. The low frequency stimulation and the burst stimulation can be delivered on similar and/or dissimilar functional elements 260 (e.g., similar or dissimilar electrode-based functional elements 260).

As described herein, apparatus 10 can be configured for treating numerous disease and disorders, such as when apparatus 10 is configured to deliver electrical or other stimulation energy to treat pain (e.g., by delivering electrical or other energy to the spine or other neural location). Apparatus 10 can be configured to stimulate tissue with various stimulation waveforms, such as those described in applicant's U.S. Provisional Patent Application Ser. No. 62/417,907, titled "Apparatus with Enhanced Stimulation Waveforms", filed Nov. 4, 2016, the content of which is incorporated herein by reference in its entirety for all purposes.

Apparatus 10 can be configured to treat neuropathy, neuralgia and/or other nerve pain that is related to: surgery; trauma; infection (e.g., a herpetic infection); and/or diabetes (e.g., diabetic neuropathy). One or more functional elements 260 can be configured to deliver stimulation energy (e.g., electrical energy, magnetic energy, light energy, thermal energy, sound energy, and/or chemical energy (e.g., energy from a drug or reagent) to nerve tissue such as tissue of the central nervous system and/or peripheral nervous system. One or more leads 265 (each comprising one or more functional elements 260) can be implanted in and/or proximate the spinal cord, the groin and/or a joint such as the hip. For example, apparatus 10 can be configured to treat one or more of: post-surgical neuralgia (e.g., following hernia repair such as a hernia repair including an implanted mesh); headache (e.g., due to occipital neuralgia); post-herpetic neuralgia; chronic pelvic and/or hip pain; knee pain; and combinations of one or more of these.

To treat pain related to hernia or hernia repair, one or more functional elements 260 (e.g., on a lead 265 and/or on a housing 210) can be positioned to stimulate tissue of the peripheral nervous system and/or the central nervous system. In some embodiments, one or more functional elements 260 are positioned to stimulate the cutaneous branch of the ilioinguinal, inguinal and/or genital branch of the genitofemoral nerves. In some embodiments, one or more functional elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these.

The apparatus of the present inventive concepts can be configured to stimulate the ilioinguinal nerve, genitofemoral nerve and/or iliohypogastric nerves, such as to ameliorate pain following hernia repair. One or more leads 265 (e.g., one or more leads 265 comprising one or more electrode-based or otherwise stimulation-based functional elements 260) can be inserted over the inguinal region (which may include the inguinal ring) to stimulate any or all three of these nerves (e.g., in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more functional elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g., the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g., transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g., percutaneous or paddle) including stimulation-based functional elements 260 can be placed over the dorsal columns, over the dorsal roots and/or in the dorsal root entry zone, in a unilateral, bilateral and/or midline fashion.

To treat occipital neuralgia, also known as C2 neuralgia, one or more functional elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more functional elements 260, can be implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more functional elements 260 are positioned to stimulate the trigeminal and/or occipital nerves. One or more leads 265 can be anchored to the fascia proximate the tissue to be stimulated.

To treat post-herpetic neuralgia (e.g., neuralgia associated with shingles), one or more functional elements 260 can be positioned to stimulate corresponding branches of the spinal nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g., using bilateral and/or unilateral stimulation) one or more of the targets listed below.

In some embodiments, the stimulated targets include the sacral nerves (roots) S2, S3 and/or S4. One or more leads 265 (e.g., each including one or more stimulation-delivering functional elements 260) can be positioned to stimulate any or all of the three roots, on a single side or both sides, in any bilateral or unilateral combination. The roots can be accessed, with the patient lying in the prone position, by positioning one or more leads 265 (e.g., percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g., in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g., fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g., through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g., fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g., voiding dysfunction). The tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g., a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e., stimulation energy delivered from inside a blood vessel to nerve tissue proximate the blood vessel), such as via the femoral vein and/or artery, each of which provide intraluminal access to many other blood vessels (e.g., using standard interventional techniques). The tibial nerve can be transvascularly stimulated by the popliteal vein and/or artery (e.g., by placing one or more functional elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat overactive bladder and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more functional elements 260 are positioned to stimulate tissue of the central nervous system or tissue and/or tissue of the peripheral nervous system to treat overactive bladder, such as to stimulate one or more nerves that control and/or are otherwise related to bladder function (e.g., to increase bladder capacity, improve bladder emptying, reduce urge incontinence and/or reduce stress incontinence). For example, one or more functional elements 260 can be positioned to stimulate tibial nerve tissue and/or sacral nerve tissue (e.g., at least the S3 nerve root) to treat overactive bladder. In some embodiments, lead 265 is constructed and arranged to be positioned along one or more locations of the tibial nerve, such as a positioning performed using percutaneous technique (e.g., when lead 265 comprises a cylindrical SCS-type lead) and/or surgical (cut-down) techniques (e.g., when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g., transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more functional elements 260 are positioned proximate (e.g., in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g., a lead 265 comprising a lead extension) can be extended underneath the skin (e.g., tunneled) to a second incision (e.g., across the flank to the lower abdomen, across the midline to the buttocks, or low back), and a third incision can be made (e.g., in the abdomen, back or buttocks) where housing 210 can be inserted and connected to lead 265. Alternatively, housing 210 can be inserted at another internal location. If lead 265 is already connected (e.g., attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g., attached in manufacturing) to housing 210, lead 265 and housing 265 are implanted. In some embodiments, a first lead 265 and a first housing 210 (pre-attached or attachable) are utilized in a dose titration or other "trialing procedure", and a second lead 265 and housing 210 (pre-attached or attachable) are implanted in the patient for subsequent treatment of the patient.

In some embodiments, one or more functional elements 260 are positioned to perform posterior tibial nerve stimulation (PTNS), also referred to as percutaneous tibial nerve stimulation, such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more functional elements 260 can be positioned to perform retrograde stimulation of the sacral nerve plexus and restore the balance between bladder inhibitory and excitatory control systems of the bladder. One or more functional elements 260 can be positioned above the ankle, proximate and/or into the tibial nerve. Implantable device 200 can deliver stimulation energy to the functional elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, system 20 is configured to deliver a series of repeated stimulation periods, such as a regimen of approximately: weekly thirty minute sessions of stimulation for twelve weeks. In some embodiments, system 20 is configured to provide daily or hourly sessions that deliver stimulation for between 10 minutes and 60 minutes. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing device 80 described hereabove in reference to FIG. 1, such as to provide power and/or date to one or more implantable devices 200 to confirm acceptable improvement of the patient's overactive bladder (e.g., successful stimulation of one or more sacral nerves, tibial nerves or other tissue), before closing an incision or otherwise fully implanting one or more implantable devices 200. In some embodiments, a temporary stimulation is provided for up to one week or up to one month. In some embodiments, one or more implantable devices 200 are left in place if the temporary stimulation period is successful or unsuccessful (e.g., left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more functional elements 260 are positioned to stimulate periurethral muscles. In some embodiments, one or more functional elements 260 are positioned to stimulate tissue of the vagina or anus. In some embodiments, one or more functional elements 260 are positioned to stimulate sphincter muscles for controlling the bladder, such as two functional elements 260 positioned on either side of the urethral orifice. In these embodiments, housing 210 can be implanted in suprapubic region or in the perineum. In some embodiments, lead 265 comprises (e.g., on a distal portion) a pessary ring comprising two functional elements 260. In some embodiments, functional elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more functional elements 260 (e.g., one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more functional elements 260 are configured to deliver energy to sacral nerve or other tissue.

In some embodiments, apparatus 10 is configured to treat fecal incontinence, overactive bladder (i.e., overactive bladder and/or urinary incontinence), and/or pelvic disorders, and implantable device 200: comprises between 1 and 16 functional elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 µsec and 240 µsec (or between 1 µsec and 200 µsec); provides electrical stimulation energy with an amplitude of approximately 0.1V to 8.5V (e.g., providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more functional elements 260 (e.g., small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratrochlear; sphenopalatine (SPG); and combinations of one or more of these.

In some embodiments, apparatus 10 is configured to treat neuralgia, such as a neuralgia resulting from surgery (e.g., groin, shoulder, lung and/or amputation), trauma and/or phantom pain, and one or more functional elements 260 are positioned to stimulate nerve tissue.

In some embodiments, apparatus 10 is configured to treat neuralgia, such as a neuralgia resulting from groin surgery (e.g., hernia or other groin surgery), and one or more functional elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more functional elements 260 are positioned to stimulate axial nerve tissue (e.g., one or more functional elements 260 positioned on a lead 265 implanted in a suprascapular location).

In some embodiments, apparatus 10 is configured to treat neuralgia, such as a neuralgia resulting from lung surgery, and one or more functional elements 260 are positioned to stimulate intercostal nerve tissue.

In some embodiments, apparatus 10 is configured to treat neuralgia, such as a neuralgia associated with carpal tunnel syndrome, and one or more functional elements 260 are positioned to stimulate median nerve tissue.

In some embodiments, apparatus 10 is configured to treat neuralgia, such as a neuralgia associated with temporomandibular joint disorder (TMJ), and one or more functional elements 260 are positioned to stimulate V2 of trigeminal nerve tissue.

In some embodiments, apparatus 10 is configured to treat neuralgia, such as a facial neuralgia, and one or more functional elements 260 are positioned to stimulate trigeminal nerve tissue.

In some embodiments, apparatus 10 is configured to treat neuralgia, such as a leg (sciatic) neuralgia, and one or more functional elements 260 are positioned to stimulate nerve tissue proximal a contributing lesion.

In some embodiments, apparatus 10 is configured to treat pelvic pain, such as interstitial cystitis and/or bladder pain, and one or more functional elements 260 are positioned to stimulate peripheral nervous system tissue (e.g., pudendal tissue and/or S-2, S-3 and/or S-4 roots) and/or central nervous system tissue (e.g., lower spinal cord and/or S3 neural foramen).

In some embodiments, apparatus 10 is configured to treat pelvic pain, such as anal pain, and one or more functional elements 260 are positioned to stimulate peripheral nerve tissue such as pudendal tissue and/or S-2, S-3 and/or S-4 roots.

In some embodiments, apparatus 10 is configured to treat subcutaneous pain, and one or more functional elements 260 (e.g., paddle electrodes) are positioned to stimulate nerve tissue.

In some embodiments, apparatus 10 is configured to treat diabetic neuropathy, such as painful diabetic neuropathy, and one or more functional elements 260 are positioned proximate the lower spinal cord (e.g., to stimulate S3 nerves) or other body location to stimulate nerve tissue.

In some embodiments, apparatus 10 is configured to treat visceral pain, angina and/or other pain, and one or more functional elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g., such that one or more functional elements 260 are positioned proximate the nerve to be stimulated). In some embodiments, lead 265 is positioned to stimulate the dorsal root ganglia to treat diabetic neuropathy (e.g., diabetic neuropathy of the hand and/or foot). Lead 265 can be implanted percutaneously and/or surgically as described herein. Lead 265 and/or one or more functional elements 260 can comprise a paddle electrode, such as one or more paddle electrodes implanted in the foot, leg and/or arm. Lead 265 and/or one or more functional elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g., to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g., each including one or more functional elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off of the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, functional element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off of the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more functional elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more functional elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 can be configured to transvascularly stimulate at least one of a median nerve, an ulnar nerve or a radial nerve, and functional element 260 can comprise one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 can be configured to transvascularly stimulate at least one of a median nerve or an ulnar nerve, and functional element 260 can comprise one or more electrodes positioned in a vessel selected from the group consisting of: brachial vein; brachial artery; and combinations of one or more of these. In some embodiments, apparatus 10 can be configured to transvascularly stimulate the radial nerve, and functional element 260 can comprise one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and functional element 260 can comprise one or more electrodes positioned in the basilic vein. In some embodiments, apparatus 10 is configured to transvascularly stimulate the ulnar nerve, and functional element 260 can comprise one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and functional element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g., a paddle lead) in the epidural space. A lead 265 can be placed such that one or more functional elements 260 (e.g., one or more electrodes) are positioned from T5-S5, such as to capture the area of pain or reduced circulation of the leg or foot. One or more functional elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more functional elements 260 (e.g., one or more electrodes attached to one or more leads 265) can be positioned to transvascularly stimulate one or more nerves, such as one or more nerves in the foot, leg and/or arm, such as when the one or more functional elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more functional elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more functional elements 260 (e.g., one or more electrodes attached to one or more leads 265) can be positioned to stimulate dorsal root ganglia that supply the following nerves (e.g., to treat the leg and/or foot): common peroneal (L4-S2); tibial (L4-S3); femoral (L2-L4); and combinations of one or more of these. One or more functional elements 260 (e.g., one or more electrodes attached to one or more leads 265) can be positioned to stimulate dorsal root ganglia that supply the following nerves (e.g., to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more functional elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g., a paddle lead) in the epidural space. One or more leads 265 can be positioned to provide transvascular stimulation of nerves in the leg or arm, such as when one or more functional elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUVA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g., which arise from C2 and C3); the greater and/or lesser auricular nerves (e.g., which also arise from C2/C3); the third (least) occipital nerve (e.g., which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g., a cylindrical SCS-type lead) can be inserted percutaneously either subcutaneously or under the muscle. Alternatively, surgical (e.g., direct cut-down) can be performed to insert lead 265 (e.g., a cylindrical lead, a paddle lead, a cuff or hemi-cuff electrode) proximate, one and/or around these nerves. Alternatively or additionally, the nerves can be accessed transvascularly as described herein (e.g., when one or more functional elements 260 are implanted in a blood vessel). Housing 210 can be implanted anywhere in the head under the skin, including: behind the ear, back of the head, the neck, in the face, and the like, where an one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more functional elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g., a paddle lead) in the epidural space. One or more leads 265 can be positioned to provide transvascular stimulation of nerves in the leg, torso and/or arm, such as when one or more functional elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, implantable device 200 has an internal battery or other power supply such that stimulation (e.g., stimulation energy and/or a stimulation agent) can be delivered to one or more locations within a patient for an extended time period (e.g., at least 1 hour, at least 1 day, at least 1 month or at least 1 year), without receiving a power transmission (e.g., as described herein from an external device such as external device 500) during that time period. In some embodiments, at least a portion of a single pulse of energy (e.g., at least a single phase) is delivered by implantable device 200 using energy provided by an internal power supply such as a battery or a capacitor. In these embodiments, data can be transmitted by one or more of an external device 500 and/or programmer 550, such as to activate or modify stimulation being delivered, with or without also transmitting power.

In some embodiments, implantable device 200 comprises one or more components configured to receive transmitted power (e.g., via an external device 500), receive transmitted data (e.g., via an external device 500 and/or programmer 550) and/or deliver stimulation (e.g., deliver stimulation energy and/or a stimulation agent).

In some embodiments, one or more implantable devices 200 are configured to deliver stimulation energy (e.g., via one or more functional elements 260 comprising an electrode) with a stimulation waveform comprising one or more high frequency signals (e.g., a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e., not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described herein. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g., a pulse comprising at least a cathodic portion and an anodic portion). In some embodiments, single or groups of pulses are provided at time-varying modes of repetition (e.g., regular intervals for a period, then a period of irregular intervals) or at regular intervals with occasional (random) spurious pulses inserted (creating a single irregular event in an otherwise regular series). Non-limiting examples of waveform variations include: a variation in frequency (e.g., frequency of one or more signals of the waveform); variation of a signal amplitude; variation of interval time period (e.g., at time period between pulses or a time period between pulse trains); variation of a pulse width; multiple piecewise or continuous variations of one of more stimulation parameters in a single pulse (e.g., multi-step, multi-amplitude in one "super-pulse"); variation of pulse symmetry (e.g., via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" such as a variation performed temporally (e.g., on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device can be configured to vary a stimulation waveform randomly, such as is described herein. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters as described herein. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g., paresthesia or other undesired condition) from the stimulation signal. In some embodiments, the amplitude of the stimulation signal can be ramped (e.g., up and/or down), a single time or multiple times (e.g., continuously or intermittently). In some embodiments, a titration procedure can be performed to "set" one or more stimulation parameters based on avoiding patient discomfort.

In some embodiments, one or more implantable devices 200 (e.g., as described hereabove in reference to FIG. 1) are configured to deliver stimulation energy (e.g., via one or more functional elements 260 comprising an electrode) with a stimulation waveform comprising one or more waveform patterns. The stimulation waveforms delivered can be configured to treat various conditions of a patient. Each stimulation waveform can comprise a series of continuous pulses, intermittent pulses, and/or spurious pulses (e.g., occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g., comprise an exponential portion), such as dynamic return pulses that exceed a minimum current (e.g., at least 1 mA, 10 mA or 50 mA) for a short duration (e.g., for approximately 1 μsec), and then decay to lower current levels (e.g., a level of approximately 100 nA), with a time constant on the order of 1 μsec to 100 μsec.

The stimulation waveforms delivered by implantable device 200 can comprise one or more high frequencies (e.g., as described herein). The stimulation waveform frequency or other stimulation parameter can be set and/or adjusted (hereinafter "adjusted") to optimize therapeutic benefit to the patient and minimize undesired effects (e.g., paresthesia or other patient discomfort). In some embodiments, a stimulation waveform is adjusted based on a signal produced by a sensor of apparatus 10 (e.g., a sensor of implantable device 200, such as a functional element 260 configured as a sensor or other sensor of implantable device 200 as described hereabove). Adjustment of a stimulation waveform parameter can be performed automatically by the implantable device 200 and/or via an external device 500 and/or programmer 550).

In some embodiments, a pulse shape can be varied, such as a pulse shape comprising: a sinusoidal geometry; a square geometry (e.g., a waveform comprising a square wave); a rectangular geometry; a triangular geometry; (e.g., symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g., anodal phase) is varied by implantable device 200.

Inter-pulse gap, the time between one or more pulses (e.g., a biphasic or other multiphasic pulse that is repeated continuously), can be varied systematically and/or randomly by implantable device 200. In some embodiments, inter-pulse gap between one or more pulses comprises zero time (i.e., a first pulse is immediately followed by a similar or dissimilar second pulse). In some embodiments, inter-pulse gap is varied systematically, such as on a routine basis (i.e., temporally) and/or varied based on a signal produced by a sensor of apparatus 10. Alternatively or additionally, inter-pulse gap can be varied randomly. such as a random variation based on a distribution (e.g., a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g., comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g., varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g., a signal comprising a modulation frequency of 1 Hz). In these embodiments, the depth of modulation would be 33%, where depth of modulation is equal to 1-[lower range/upper range]. In some embodiments, amplitude of delivered current fluctuates between 1 mA and 3 mA (i.e., a depth of modulation of 66%), while in other embodiments, current fluctuates between 0 mA and 3 mA (e.g., a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g., a quiescent period) can be included. In some embodiments, controller 250 comprises one or more reconfigurable stimulation blocks including one or more Howland or other current sources. The one or more current sources (e.g., two or more current sources) can each be attached to a functional element 260 (e.g., in a monopolar configuration when the current source is also connected to housing 210 or in a bipolar configuration when the current source is connected to a pair of functional elements 260). Alternatively, controller 250 can comprise one or more current sources that are attached to a matrix of switches that selectively connect the one or more current sources to multiple functional elements 260 (e.g., connect a single current source to 2, 4, 8, 12 or 16 electrodes). In some embodiments, controller 250 is configured such that a stimulation waveform signal provided to the current source passes through a capacitor (e.g., capacitor C1 shown), the capacitor providing DC balance.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 μsec and 1 msec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of: sinusoid; square, rectangle; triangle (symmetric or asymmetric); trapezoid; sawtooth; ramp (e.g., a linear ramp); exponential curve; piece-wise step function; and combinations of one or more of these. Implantable device 200 can deliver a train or burst stimulation waveform with an inter-pulse gap less than inter-train period (e.g., as shown in FIG. 30A). The inter-pulse gap can be relatively constant or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200 can deliver a train stimulation waveform with an inter-pulse gap between 1 μsec and 1 second. Implantable device 200 can deliver a burst stimulation waveform with an inter-train period between 1 μsec and 1 second. Implantable device 200 can deliver a burst stimulation waveform with an inter-burst period between 20 μsec and 24 hours. The inter-burst period can be relatively constant or it can be varied, such as when implantable device 200 randomly varies the inter-burst period or varies the inter-burst period systematically. In some embodiments, inter-burst period is varied by the user, such as via a user using controller 550. In these embodiments, user activation can be regulated with one or more safeguards or other limits such as those incorporated into patient controlled analgesia devices. The inter-train period can be varied between 1 μsec and 24 hours. Implantable device 200 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g., linear ramp); and combinations of one or more of these. Implantable device 200 can deliver a train and/or burst stimulation waveform with a train ramp duration or burst ramp duration between 1 μsec to 10 minutes. Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period as described herein. The amplitude of the signal contained in these quiescent period may be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g., electrical energy comprising a low frequency signal) and burst stimulation; burst stimulation (e.g., burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more functional elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters. The stimulation parameters can be varied to optimize (e.g., balance the benefits of) therapeutic benefit, system efficiency, stimulation efficiency, avoidance and/or reduction of paresthesia, and/or reduction of charge.

Figure 1A:
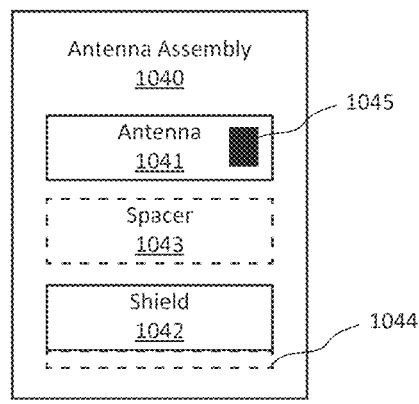
FIG. 1A is a schematic view of an antenna assembly comprising an antenna and a shield, consistent with the present inventive concepts.

Referring now to FIG. 1A, an antenna assembly comprising an antenna and a shield is illustrated consistent with the present inventive concepts. Antenna assembly 1040 comprises a transmitting/receiving antenna, antenna 1041, and at least one shielding element (e.g., an electromagnetic shielding element), shield 1042. In some embodiments, antenna assembly 1040 is of similar construction and arrangement to one or more of antenna assemblies 1040 described herebelow in reference to FIGS. 2A-2F. In some embodiments, one or more external antennas 540 have the construction and arrangement of one or more antenna assemblies 1040 described herein, such as to transmit power and/or data and/or to receive power and/or data, also as described herein. Alternatively or additionally, one or more implantable antennas 240 can have the construction and arrangement of one or more antenna assemblies 1040 described herein.

Antenna 1041 can comprise one or more antennas selected from the group consisting of: patch antenna; slot antenna; array of antennas; a loop antenna (e.g., a concentric loop antenna); antenna loaded with reactive elements; dipole antenna; quadrupole antenna; multi-pole antenna; polarizable antenna; selectable conductors that form an antenna; and combinations of one or more of these. Antenna 1041 can comprise an antenna element 1045 which is the portion of antenna 1041 which sends and/or receives the wireless transmissions. Antenna element 1045 can comprise one, two or more elements selected from the group consisting of: a wire; a conductive element; a conductive trace (e.g., a trace on a printed circuit board or other substrate); a first conductive trace on one side of a substrate and a second conductive trace on the opposite side of a substrate; a first conductive trace on a first substrate, and a second conductive trace on a second substrate; and combinations thereof. In some embodiments, antenna element 1045 comprises a first conductive trace on one side of a substrate and a second conductive trace on the opposite side of a substrate, where the first and second traces are connected by one or more vias passing through the substrate, such as a connection made by at least 10 vias, or at least 100 vias, such as is described herebelow in reference to FIGS. 4E-F. In some embodiments, each antenna element 1045 comprises a conductive trace with an impedance below 10 mOhm, or an impedance below 20 mOhm. In some embodiments, antenna 1041 comprises three or more traces positioned in multiple layers of a printed circuit board, such as three or more traces connected with vias. Antenna 1041, spacer 1043, and shield 1042 determine basic properties of the antenna assembly 1040, including the inductance of antenna 1041, the quality factor Q, the bandwidth of the wireless communication link, and the matching network connected to antenna 1041. The parameters of elements 1041, 1042, and 1043 can be optimized for the desired performance of system 10. For example, a configuration with reduced inductance increases the required capacitance in the matching network, which reduces the sensitivity of the matching network to small variations in capacitance.

Shield 1042 can be positioned on one side of antenna 1041, while a different, second side of antenna 1041 faces toward an area to which antenna 1041 receives power and/or data and/or transmits power and/or data. Shield 1042 can be configured to reduce losses or loading effects caused by neighboring metallic and/or electrically conductive components (e.g., components of the same device or another device that can cause undesired loading, undesired coupling, and/or parasitic effects, "interfering components" herein). Shield 1042 can be configured to enhance the performance of one or more antennas 1041. Shield 1042 can be configured to allow miniaturization of one or more apparatus 10 components (e.g., one or more components of an external device 500 or implantable device 200 into which shield 1042 is positioned), such as by desensitizing the miniaturized components to environmental disturbances (e.g., electromagnetic radiation) while preventing or at least reducing degradation in system performance. In some embodiments, shield 1042 is configured to improve system performance, such as by providing magnetic field magnification to one or more antennas 1041. Shield 1042 can be configured to shield one or more components of apparatus 10 and/or other electronic components in the environment surrounding the one or more transmitting antennas 1041 (e.g., at least a portion of the surrounding environment, such as to shield one or more electronic components on the side of shield 1042 opposite antenna 1041) from undesired radiations from one or more antennas 1041, which can reduce electromagnetic shielding or filtering requirements of the remainder of apparatus 10.

Shield 1042 can comprise ferrite (e.g., high-frequency ferrite) or other material with a property selected from the group consisting of: high magnetic permeability (u') at the operating frequency of the antenna 1041 transmission (e.g., a high frequency, such as a frequency above 1 MHz, or above 10 MHz); low magnetic loss tangent (u"/u') at the operating frequency of the antenna 1041 transmission (e.g., a high frequency, such as a frequency above 1 MHz, or above 10 MHz); low conductivity at the operating frequency of the antenna 1041 transmission (e.g., a high frequency, such as a frequency above 1 MHz, or above 10 MHz); and combinations of one or more of these. In some embodiments, transmissions from antenna 1041 are performed at an operating frequency between 1 MHz and 100 MHz, between 1 MHz and 50 MHz, or between 10 MHz and 50 MHz. In some embodiments, transmissions from antenna 1041 are performed at an operating frequency of between 38.5 Mhz and 42.5 Mhz, such as at an operating frequency of approximately 40.5 Mhz or 40.68 Mhz, or an operating frequency between 40.66 MHz and 40.7 MHz. In some embodiments, shield 1042 comprises a magnetic permeability (u') of greater than or equal to 40. In some embodiments, shield 1042 comprises a magnetic loss tangent (u"/u') less than or equal to 0.025 (e.g., u" is less than 1 when u' is equal to 40). In some embodiments, shield 1042 comprises a conductivity less than or equal to 1e−3 S/m, or less than or equal to 1e−5 S/m.

In some embodiments, shield 1042 comprises a thickness between 0.1 mm and 5 mm, such as a thickness between 0.5 mm and 2 mm. Shield 1042 can comprise a coating or other layer of material, layer 1044, positioned on the side of the shielding layer opposite the side facing antenna 1041, to increase shielding of unwanted radiation. Layer 1044 can comprise one or more electromagnetic energy absorbing material (e.g., radiofrequency energy absorbing material), and/or conductive material. In some embodiments, shield 1042 comprises one or more holes or slots (e.g., to reduce weight of shield 1042), such as holes 1048 described herebelow in reference to FIG. 5A. The holes 1048 can be spaced in a way to minimize reduction in performance of shield 1042, such as at a spacing that is smaller than a wavelength of one or more electromagnetic signals intended to be shielded by shield 1042. In some embodiments, holes, slots and/or other recesses or openings ("holes" herein) can be used to align and/or position antenna 1041, spacer 1043, shield 1042 and/or another component of antenna assembly 1040. In some embodiments, holes can be used to allow passage of a mechanical or electrical element (e.g., to allow an electrical connection to pass through shield 1042).

Figure 2A:
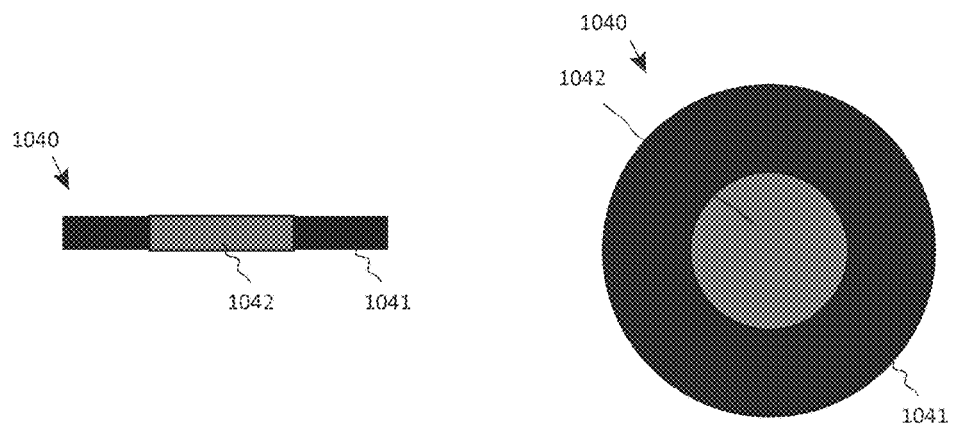
FIGS. 2A-2F are views of various configurations of antenna assemblies, consistent with the present inventive concepts.
Figure 2B:
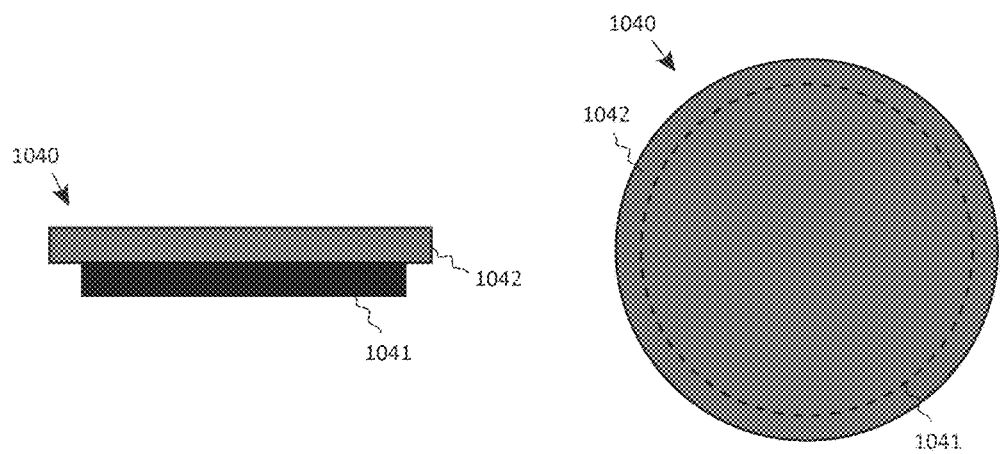
Figure 2C:
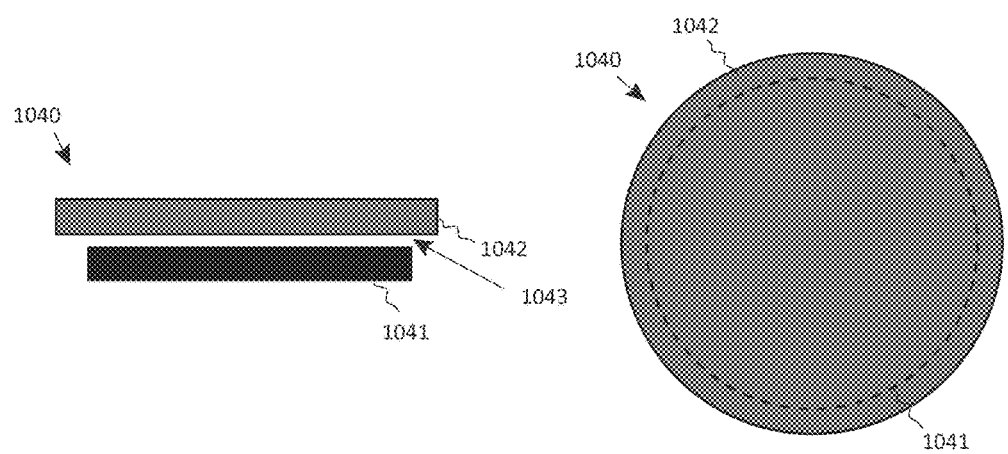
Figure 2D:
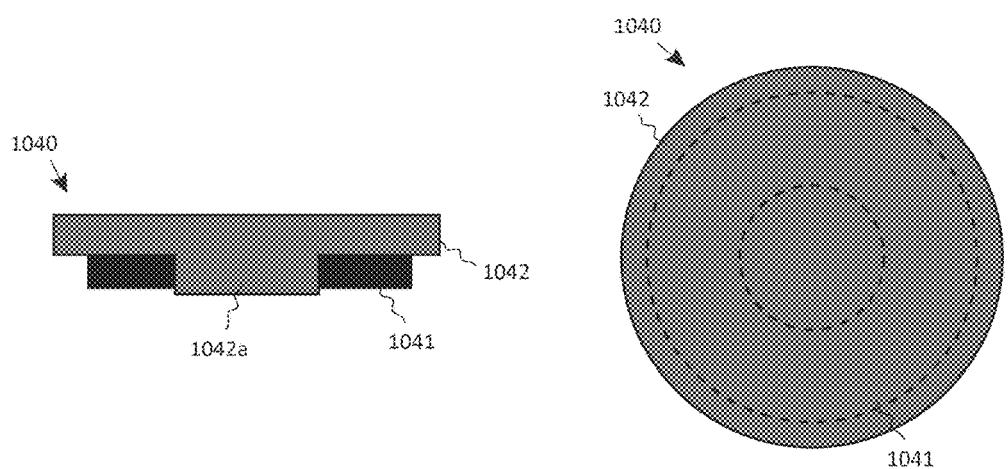
Figure 2E:
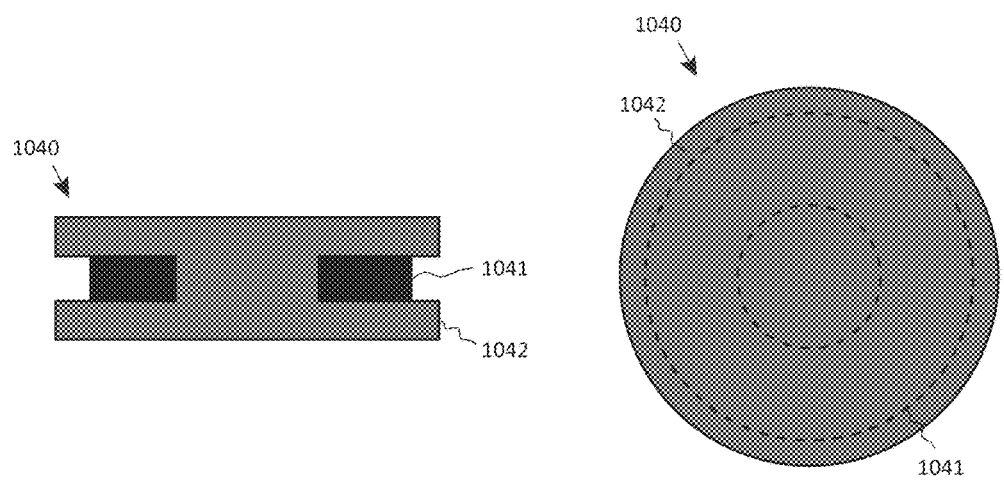

Shield 1042 can comprise a relatively flat geometry (e.g., a disk or plate that resides in essentially a single plane), or a multi-planar geometry, examples of each of which are described herebelow in reference to FIGS. 2A-F. Shield 1042 can comprise a projecting portion, such as a projecting portion that extends into a recess or opening of antenna 1041, such as is shown in FIGS. 2D and 2E.

Shield 1042 can be configured to increase directivity of one or more antennas 1041 and/or to focus the electromagnetic transmissions of one or more antennas 1041, such as by limiting the directions to which antenna 1041 transmits.

In some embodiments, the periphery of shield 1042 fully covers, and can extend beyond the periphery of antenna 1041. In some embodiments, the periphery of shield 1042 covers a majority of the surface area (as defined by the periphery) of antenna 1041, such as to shield at least 50%, at least 70% or at least 80% of the surface area of antenna 1041.

In some embodiments, antenna assembly 1040 further includes an optional space-providing element, spacer 1043, which can comprise one or more spacers positioned between antenna 1041 and shield 1042, between antenna 1041 and another component of system 10, and/or between shield 1042 and another component of system 10.

Spacer 1043 may comprise a simple gap (e.g., a gap occupied by air or other gas), or a solid or liquid material. Spacer 1043 may comprise a thickness (e.g., a spacing) of between 0.01 mm and 5 mm, between 0.25 mm and 1 mm, or approximately 0.8 mm. Spacer 1043 can comprise an adjustable spacer, such as when spacer 1043 comprises a compressible material. Adjustment of the spacing via spacer 1043 can be used to tune the antenna assembly 1040 performance. Spacer 1043 can be constructed of non-conductive dielectric materials, or other materials configured to minimize adverse impact on antenna 1041 performance. Spacer 1043 can comprise a printed circuit board or other substrate, or a substrate of the present inventive concepts (e.g., substrate 211 or 511) can comprise spacer 1043. In some embodiments, spacer 1043 comprises a low dielectric loss tangent, such as a dielectric loss tangent less than or equal to 0.05, such as less than or equal to 0.02 or less than or equal to 0.005. In some embodiments, spacer 1043 comprises glass-reinforced epoxy laminate (e.g., FR-4) and/or acetal (e.g., Delrin® material provided by Dupont). Spacer 1043 can comprise one or more spacers, and each spacer can comprise one or more materials. In some embodiments, a first spacer 1043 (e.g., a spacer comprising a first material) is positioned above antenna 1041, and a second spacer 1043 (e.g., a spacer comprising a second, different material) is positioned below antenna 1041.

Antenna assembly 1040 can comprise one or more antennas 1041, such as an assembly 1040 comprising one or more antennas 1041, one or more shields 1042, and an optional one or more spacers 1043. Multiple antenna assemblies 1040 and/or multiple antennas 1041 (e.g., in a single antenna assembly 1040) can be configured as independent antennas or as an array of electrically connected antennas (e.g., capacitively connected antennas), such as is described herebelow in reference to FIG. 7. Multiple antennas assemblies 1040 and/or multiple antennas 1041 can be configured as a multi-directional antenna array (e.g., a 2-directional or 3-directional array).

Figure 2F:
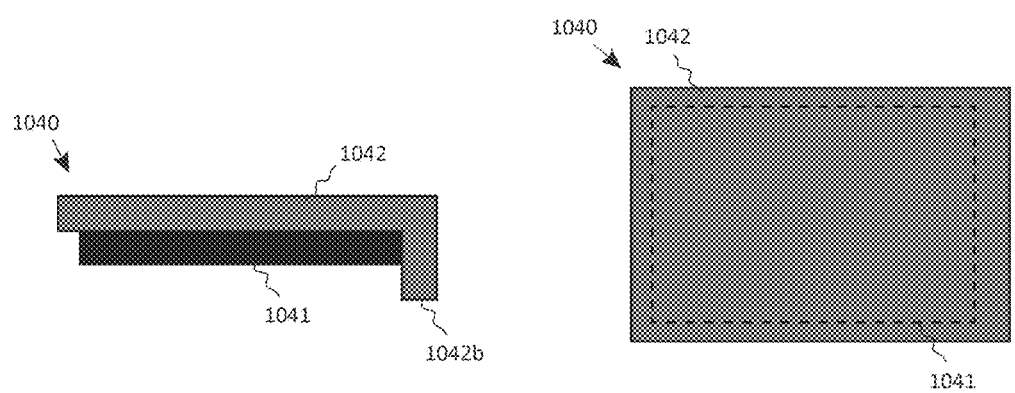

Referring now to FIGS. 2A-2F, views of various configurations of antenna assemblies are illustrated, consistent with the present inventive concepts. The antenna assemblies 1040 of FIGS. 2A-2F can be of similar construction and arrangement to antenna assembly 1040 described hereabove in reference to FIG. 1A. Each of the antennas 1041 of FIGS. 2A-2E are shown with a circular shaped periphery, and antenna 1041 of FIG. 2F is shown with a rectangular shaped periphery. In should be understood that each antenna 1041 can comprise a circular or a non-circular periphery, such as a rectangular, trapezoidal or other non-circular shape. Each of the antennas 1041 can comprise an opening (e.g., as shown in FIGS. 2A, 2D and 2E), which can comprise a circular shaped opening or a non-circular shaped opening (e.g., a rectangular, trapezoidal or other non-circular shaped opening). Each of the shields 1042 of FIGS. 2A-2E are shown with a circular shaped periphery, and shield 1042 of FIG. 2F is shown with a rectangular shaped periphery. It should be understood that each shield 1042 can comprise a circular or a non-circular shaped periphery, such as a rectangular, trapezoidal or other non-circular shape. Each of the shields 1042 can comprise a shape of its periphery (or at least the periphery of an extension or other portion of shield 1042) that relatively matches the shape of an opening of antenna 1041 into which at least a portion of shield 1042 can be positioned (e.g., a circular shaped shield 1042 positioned in a circular shaped opening of antenna 1041 as shown in FIGS. 2A, 2D and 2E). Each of the antenna assemblies 1040 can comprise a spacer, such as a spacer positioned between antenna 1041 and shield 1042, such as spacer 1043 described herein.

In FIG. 2A, side sectional and top views of an antenna assembly 1040 are shown, including an antenna 1041 with an open inner portion, and a shield 1042 positioned (e.g., fully positioned) in the open inner portion of antenna 1041.

In FIG. 2B, side and top views of an antenna assembly 1040 are shown, in which antenna 1041 and shield 1042 are positioned in a side-by-side arrangement, such as when one side of antenna 1041 contacts one side of shield 1042 (i.e., minimal or no gap is present). In some embodiments, the periphery of shield 1042 fully covers, and can extend beyond (as shown in FIG. 2B) the periphery of antenna 1041. In some embodiments, the periphery of shield 1042 covers a majority of the surface area (as defined by the periphery) of antenna 1041, such as to shield at least 50%, at least 70% or at least 80% of the surface area of antenna 1041.

In FIG. 2C, side and top views of an antenna assembly 1040 are shown, in which antenna 1041 and shield 1042 are positioned in a side-by-side arrangement with a gap between the two components. In some embodiments, one or more spacing elements, spacer 1043 is positioned between antenna 1041 and shield 1042. In some embodiments, spacer 1043 comprises air or other gas that is positioned between antenna 1041 and shield 1042 (e.g., when antenna 1041 and shield 1042 are fixed or otherwise maintained with the separation between the two, via one or more fixation elements not shown). In some embodiments, the periphery of shield 1042 fully covers, and can extend beyond (as shown in FIG. 2C) the periphery of antenna 1041.

In FIG. 2D, side sectional and top views of an antenna assembly 1040 are shown, in which shield 1042 includes an extending portion 1042a which is positioned within an opening of antenna 1041. In some embodiments, the periphery of the top portion of shield 1042 fully covers, and can extend beyond (as shown in FIG. 2D) the periphery of antenna 1041.

In FIG. 2E, side sectional and top views of an antenna assembly 1040 are shown in which shield 1042 comprises an "H" shape that essentially covers a top and bottom surface of antenna 1041, as well as extends through an opening of antenna 1041. In some embodiments, the periphery of the top surface of shield 1042 and/or the periphery of the bottom surface of shield 1042 fully covers the periphery of the associated top and bottom surfaces of antenna 1041, and can extend beyond the periphery of those surfaces (as shown in FIG. 2E).

In FIG. 2F, side sectional and top views of an antenna assembly 1040 are shown in which shield 1042 comprise a flange portion 1042b which extends around at least a portion of the periphery of antenna 1041.

Figure 3:
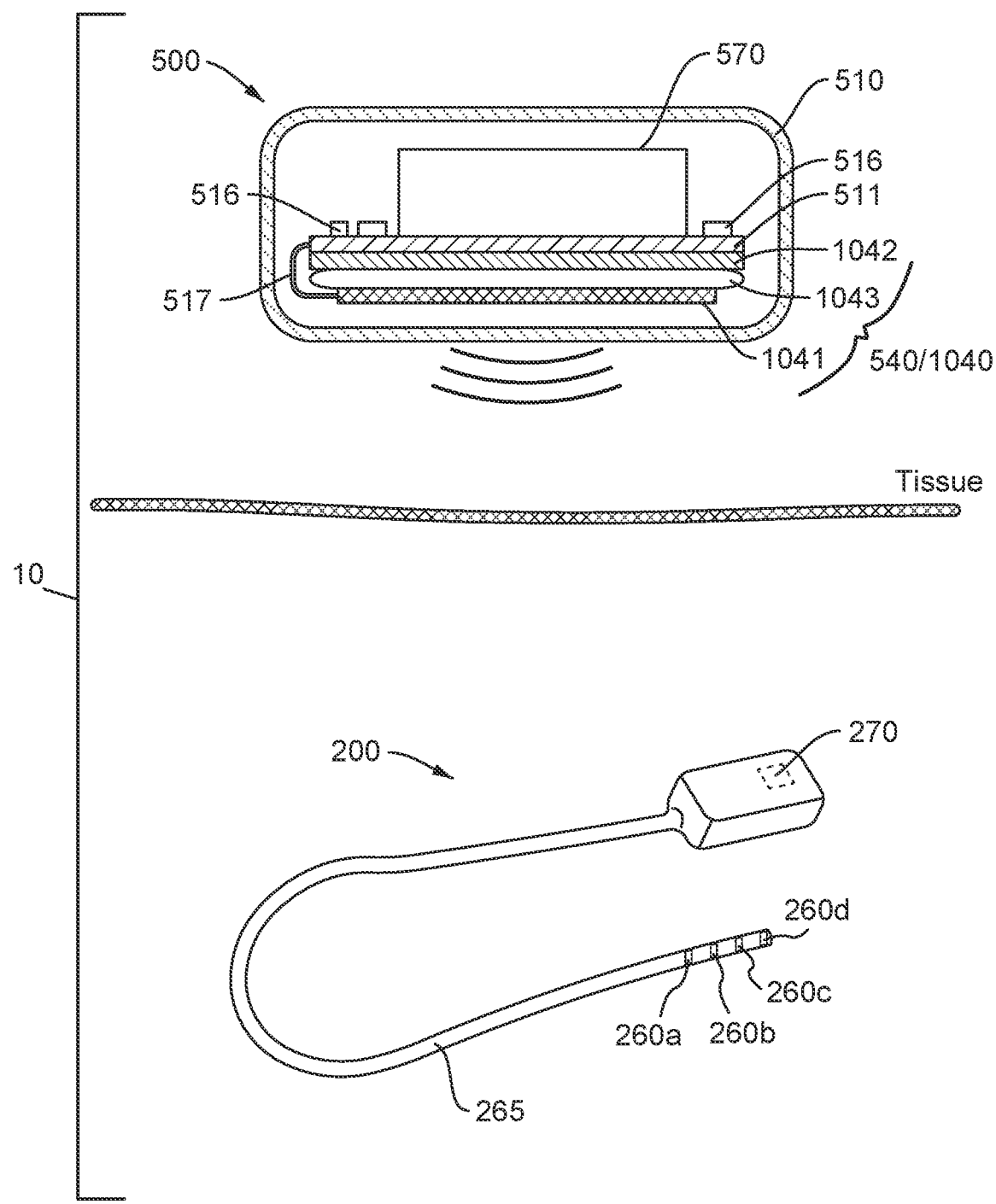
FIG. 3 is a schematic anatomical view of a medical apparatus comprising an external system including a shielded antenna assembly, consistent with the present inventive concepts.

Referring now to FIG. 3, a schematic anatomical view of a medical apparatus comprising an external system including a shielded antenna assembly is illustrated, consistent with the present inventive concepts. Apparatus 10 comprises at least one implantable device 200, and an external control device such as external device 500. Apparatus 10, implantable device 200, and/or external device 500 can be of similar construction and arrangement to similar components of apparatus 10 described hereabove in reference to FIG. 1.

Implantable device 200 can comprise an implantable battery, capacitor or other power source (e.g., energy storage assembly 270 shown and described hereabove in reference to FIG. 1), such as a power source configured to provide stimulation energy that is delivered by one or more functional elements 260 of lead 265 (e.g., one or more electrode-based or other stimulation delivering functional elements 260). In the embodiment shown in FIG. 3, implantable device 200 includes four functional elements 260*a*-*d*, however more or fewer functional elements 260 can be included (e.g., 1-32 functional elements configured to deliver electrical or other stimulation energy).

Implantable device 200 and energy storage assembly 270 can be configured to deliver stimulation energy for a prolonged period of time (e.g., at least 1 hour, at least 1 day, at least 1 month or at least 1 year), without receiving a wired or wireless power transmission from another source (e.g., the wireless power transmission described hereabove from an external device such as external device 500) during that time period. In some embodiments, energy storage assembly 270 can comprise a battery or capacitor configured to provide (e.g., store) at least 1 mWh of energy, or at least 1 Wh of energy. In some embodiments, energy storage assembly 270 is configured to provide less than 1 mWh of energy (e.g., to provide short term power in embodiments where implantable device 200 receives wired or wireless power from a separate device). In some embodiments, implantable device 200 is configured to deliver one or more stimulation waveforms comprising a waveform shape as described hereabove in reference to FIG. 1, or as described in applicant's U.S. Provisional Patent Application Ser. No. 62/417,907, titled "Apparatus with Enhanced Stimulation Waveforms", filed Nov. 4, 2016. In some embodiments, the implantable device 200 of FIG. 3 is configured to deliver one or more stimulation waveforms in which one or more stimulation parameters are varied, such as via a random variation. In some embodiments, external device 500 wirelessly transmits data (e.g., programming commands) through the patient's skin, to one or more implantable devices 200 that have been implanted. In some embodiments, external device 500 wirelessly transmits power (e.g., via an RF signal or inductive coupling) through the patient's skin to one or more implantable devices 200 that have been implanted, such as a power transfer that occurs at intervals of at least 1 day, 1 week, 1 month or 1 year. Alternatively, external device 500 transmits power to one or more implantable devices 200 relatively continuously, as described hereabove in reference to FIG. 1.

External device 500 comprises housing 510 which surrounds multiple components and/or assemblies of external device 500, such as power supply 570 (e.g., including one or more batteries, capacitors or other energy storage components) and substrate 511. One or more electronic components 516 can be attached to substrate 511, and similarly electrically connected via one or more conductive traces of substrate 511 (e.g., when substrate 511 comprises one or more single or multiple layer printed circuit boards). Power supply 570 can be positioned (e.g., attached) on a top surface of substrate 511 as shown, and can be electrically connected to one or more conductive traces of substrate 511. In some embodiments, power supply 570 can at least partially extend into substrate 511 (e.g., extend into a recess or hole of substrate 511). In some embodiments, power supply 570 comprises a user-replaceable battery. Alternatively, power supply 570 can comprise a rechargeable power source (e.g., a rechargeable battery). In these embodiments, power supply 570 can be configured to be wirelessly recharged (e.g., via inductive charging and/or wireless power received by one or more antennas 1041 of external device 500).

External device 500 further comprises an antenna 540, which can comprise an antenna assembly 1040 as described herein. Antenna assembly 1040 shown in FIG. 3 includes a shield 1042 positioned on a bottom surface of substrate 511, a spacer 1043 positioned on a bottom surface of shield 1042, and an antenna 1041 positioned on a bottom surface of spacer 1043. Antenna 1041 comprises one or more antenna elements 1045, not shown but such as is described herein. Antenna 1041 is electrically connected to substrate 511 via an electrical connector, connector 517 (e.g., a flexible conduit as shown). Connector 517 can comprise one or more connecting components, such as: a cable; a ribbon cable; a flex circuit; a side-connector (e.g., a connector that electrically attaches to two circuit boards); a compressible connector (e.g., a connector that is positioned between two circuit boards); and combinations of one or more of these. In some embodiments, antenna assembly 1040 is electrically connected to substrate 511 (e.g., to components 516 electrically connected to substrate 511) as described herebelow in reference to FIGS. 4A-C.

In some embodiments, the periphery of shield 1042 fully covers, and can extend beyond (as shown in FIG. 3) the periphery of antenna 1041, such as to provide shielding and/or improved antenna performance as described herein. In the configuration and layout of antenna assembly 1040 shown in FIG. 3, shield 1042 is positioned such than antenna 1041 is shielded from deleterious effects of components 516 and other electromagnetic field generating elements positioned above the top side of shield 1042, as described herein. Alternatively or additionally, this orientation improves transmissions (e.g., power and/or data transmissions) of antenna 1041 to implantable device 200, also as described herein.

Figure 4A:
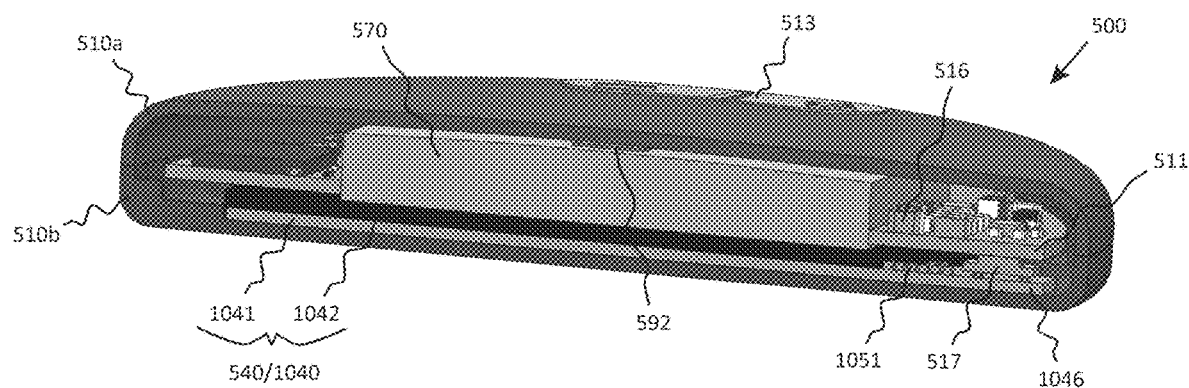
FIGS. 4A-4C are an assembled, sectional, perspective view, an exploded perspective view and an exploded side view of an external system including a shielded antenna assembly, consistent with the present inventive concepts.
Figure 4B:
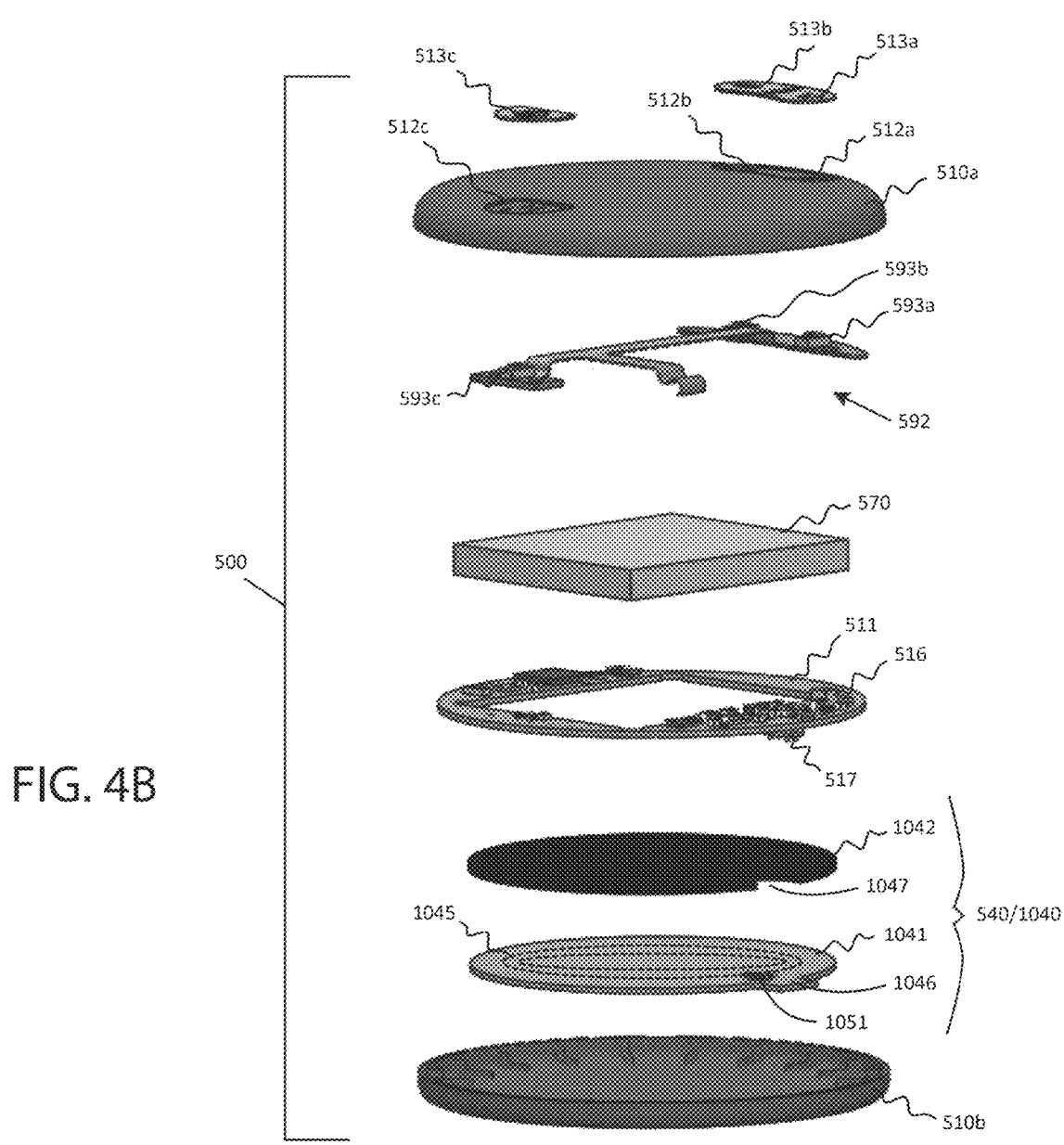
Figure 4C:
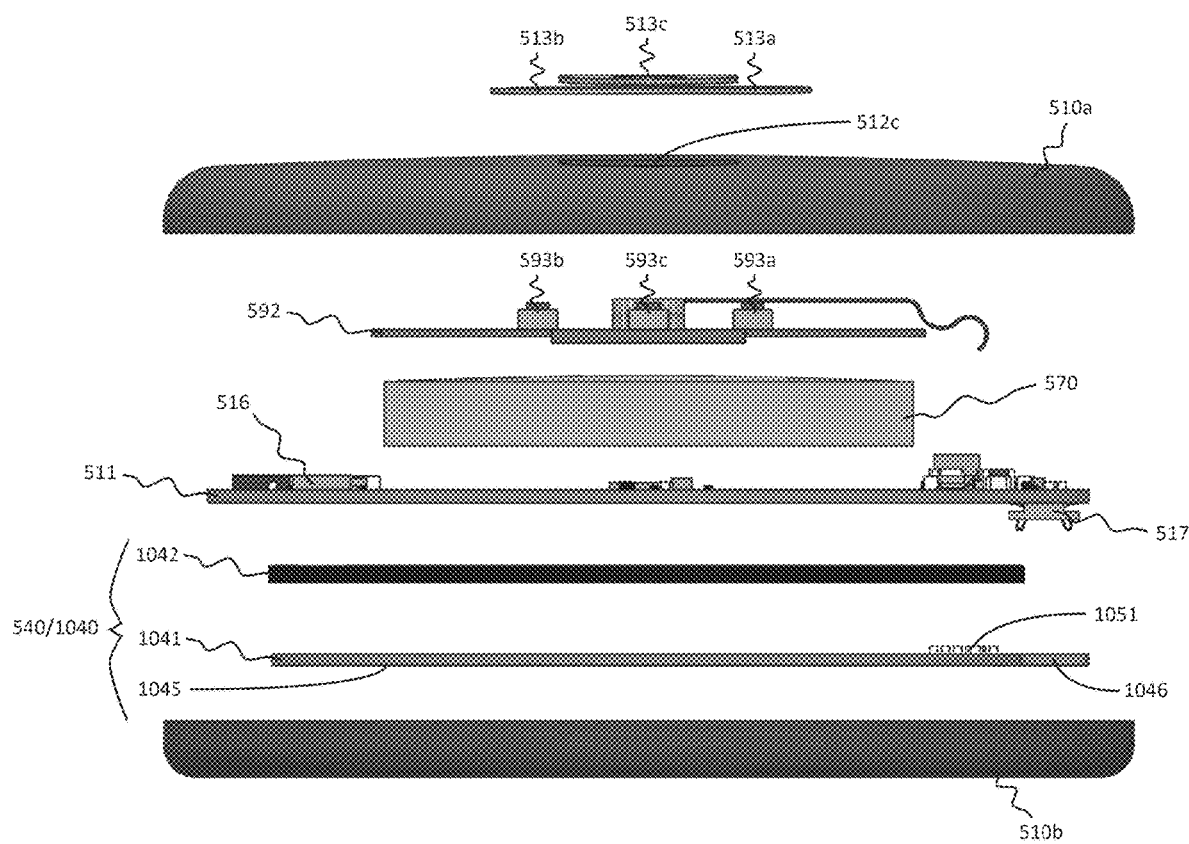

Referring now to FIGS. 4A-C, an assembled, sectional, perspective view, an exploded perspective view, and an exploded side view of an external system including a shielded antenna assembly are illustrated, consistent with the present inventive concepts. External device 500 can be of similar construction and arrangement and include similar components to external device 500 described hereabove in reference to FIG. 1. External device 500 comprises housing 510 which includes top portion 510*a* and bottom portion 510*b*. Top portion 510*a* and bottom portion 510*b* can be fixedly attached to each other via one or more attachment elements such as adhesive and/or via one or more attachment processes such as welding, such as to provide a sufficient seal to prevent a significant amount of contaminants from passing between the mating surfaces of top portion 510*a* and bottom portion 510*b*. Housing 510, when assembled, surrounds multiple components and/or assemblies of external device 500, such as power supply 570 (e.g., including one or more batteries, capacitors or other energy storage components) and substrate 511. One or more electronic components 516 can be attached to substrate 511, and similarly electrically connected via one or more conductive traces of substrate 511 (e.g., when substrate 511 comprises one or more single or multiple layer printed circuit boards). Power supply 570 can be positioned (e.g., attached) on a top surface of substrate 511 as shown, and can be electrically connected to one or more conductive traces of substrate 511. Housing 510 can comprise a battery door, not shown, such as to allow replacement of power supply 570.

External device 500 can comprise an assembly, strap assembly 592 which can include a flexible or rigid printed circuit, and can have a first end and a second end that attach to substrate 511 and maintain the position of power supply 570 relative to substrate 511. In some embodiments, strap assembly 592 and/or substrate 511 comprise one or more switches (e.g., membrane or pushbutton electrical switches), such as switches 593a-c shown. Housing 510 can comprise one or more user accessible buttons, buttons 512a-c which are operably positioned to correspondingly activate switches 593a-c, respectively, when buttons 512a-c are depressed. In some embodiments, external device 500 further comprises one or more covers surrounding (e.g., above) buttons 512a-c, such as covers 513a-c shown. Covers 513a-c can comprise rigid and/or flexible covers, such as covers configured to prevent contaminants from passing through housing 510 at buttons 512a-c.

External device 500 comprises an external antenna 540 comprising antenna assembly 1040 including antenna 1041 and shield 1042. Antenna assembly 1040 can comprise a similar construction and arrangement to any antenna assembly 1040 described herein. Antenna assembly 1040 comprises antenna element 1045, which comprises one or more antenna elements as described herein. In some embodiments, the antenna assembly of FIGS. 4A-C further comprises a spacing element (e.g., positioned between antenna 1041 and shield 1042), not shown but such as spacing element 1043 described herein. Shield 1042 is positioned between antenna 1041 and one or more electronic components of external device 500 (e.g., components 516). In the configuration and layout of antenna assembly 1040 shown in FIGS. 4A-C, shield 1042 is positioned such than antenna 1041 is shielded from deleterious effects of components 516 and other electromagnetic field generating elements positioned above the top side of shield 1042, as described herein. Alternatively or additionally, this orientation improves transmissions (e.g., power and/or data transmissions) of antenna 1041 to implantable device 200, also as described herein.

In some embodiments, antenna assembly 1040 comprises a laminate assembly comprising multiple stacked substrates (e.g., one or more substrates comprising FR4), such as an assembly comprising one or more printed circuit boards onto which one or more antennas 1041 and/or other components are mounted and/or electrically connected. In some embodiments, one or more substrates, or portions of substrates, function as spacer 1043 (not shown). In some embodiments, antenna 1041 comprises multiple conductors (e.g., multiple antenna elements 1045) positioned on different layers of the laminate assembly (e.g., copper traces separated by a dielectric layer), such as is described herebelow in reference to FIGS. 4D-E.

Antenna assembly 1040 can be electrically connected to substrate 511 (e.g., electrically connected to one or more components 516 of substrate 511) via an electrical connector, connector 517, a compressible connector positioned between substrate 511 and antenna 1041. In alternative embodiments, connector 517 comprises a flexible cable operably attached to antenna assembly 1040 and substrate 511 (e.g., as shown in FIG. 3) and/or a clip connector connected to the sides of antenna 1041 and substrate 511. In some embodiments, antenna 1041 comprises a projection, tab 1046 shown, such as a tab including a connecting portion to mate with connector 517. In some embodiments, shield 1042 can comprise a cutout 1047, and connector 517 can pass through cutout 1047.

In some embodiments, antenna assembly 1040 comprises electronic componentry 1051, such as one or more electronic components configured as a matching network for antenna 1041. In these embodiments, shield 1042 can comprise cutout 1047 shown, into which components 1051 can extend (e.g., to create clearance for components 1051 to allow shield 1042 to be positioned closer to antenna 1041). Antenna assembly 1040 can comprise a matching network that includes a tuning element, such as an adjustable capacitor. The tuning element can comprise a capacitor with a quality factor that is high, such as to minimize degradation of performance of antenna assembly 1040. Tuning of antenna assembly 1040 can be performed using a manufacturing fixture (e.g., a tuning performed prior to final assembly of antenna assembly 1040).

Figure 4D:
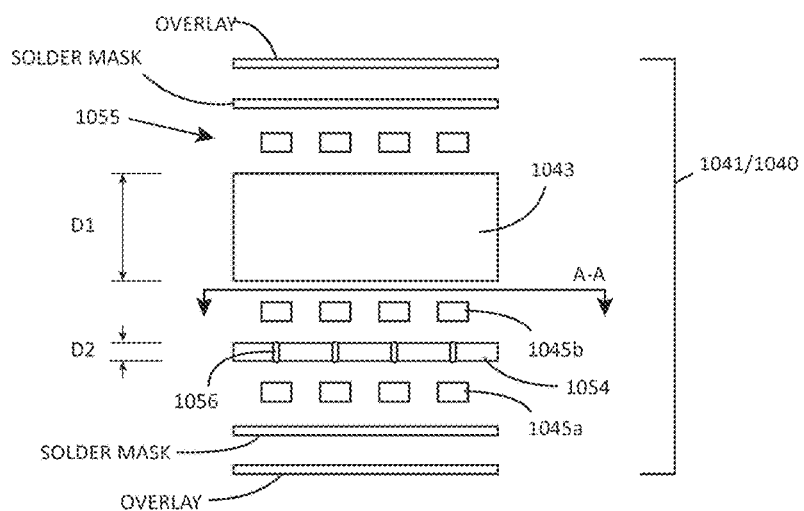
FIG. 4D is a side, schematic view of a laminate antenna assembly comprising multiple antenna elements on different layers of the laminate, consistent with the present inventive concepts.

Referring now to FIG. 4D, a side, schematic view of a laminate antenna assembly comprising multiple antenna elements on different layers of the laminate is illustrated, consistent with the present inventive concepts. Antenna assembly 1040 comprises an antenna 1041 comprising at least two antenna elements, 1045a and 1045b. Antenna assembly 1040 can be of similar construction and arrangement to any antenna assembly described herein. Antenna elements 1045a and 1045b are attached to the bottom and top side, respectively, of substrate 1054. In some embodiments, substrate 1054 comprises a thickness (D2 as shown) of approximately 100 μm, and antenna elements 1045a-b each comprise 2 ounce copper traces. The thickness D2 of substrate 1054 can be chosen to determine a desired separation distance between two antenna elements 1045. In some embodiments, antenna elements 1045a and 1045b comprise loop antennas, such as loop antennas with relatively similar dimensions that are positioned relatively aligned with each other on substrate 1054, such as is described herebelow in reference to FIGS. 4E-F. Antenna assembly 1040 can further comprise a solder mask layer, and/or an overlay layer, positioned below antenna 1045a as shown in FIG. 4D. Antenna assembly 1040 can further comprise spacer 1043, trace layer 1055, a solder mask layer, and/or an overlay layer, also as shown in FIG. 4D. Spacer 1043 comprises thickness D1, which can comprise a thickness of approximately 0.8 mm or other thickness such as a thickness described hereabove in reference to spacer 1043 of FIG. 1A. Trace layer 1055 can be positioned on spacer 1043 (e.g., when spacer 1043 comprises FR4 or other printed circuit board material). Trace layer 1055 can be electrically connected to the one or more antenna element 1045 via an electrical cable, connector and/or via (e.g., a via through spacer 1043). Trace layer 1055 can comprise one or more conductive pads (conductive pads 1057 shown in FIG. 4E), such as to mate with an electrical connector, such as connector 517 described herein. One or more components, not shown but such as components 1051 described herein, can be attached and electrically connected to trace layer 1055, such as when the components are configured as a matching network for antenna 1041 (e.g., collectively for antenna elements 1045).

In some embodiments, the laminate antenna assembly 1040, including two antenna elements 1045a-b as shown, comprises a thickness of approximately 0.8 mm, or a thickness of less than 1.2 mm, such as to minimize the size of the associated housing 510 or 210 surrounding antenna assembly 1040.

In some embodiments, antenna 1041 comprises multiple antenna elements 1045 (e.g., element 1045a-b shown) that are electrically attached via one or more vias that pass through each substrate separating the antenna elements 1045 (e.g., substrate 1054 including vias 1056 as shown), such as a connection including at least 10 vias, at least 50 vias, at least 100 vias, at least 500 vias, or at least 1000 vias that pass through each substrate. All or a majority of the vias (e.g., vias 1056) can be limited to placement in the loop portion of the associated antenna elements 1045. Addition of the multiple vias to connect antenna elements 1041 on either side of a substrate reduces the series resistance of the antenna (e.g., an antenna loop), thereby reducing energy loss during use (e.g., to improve battery life and result in other apparatus 10 efficiencies). This reduction in resistance is achieved by increasing the volume of electrically parallel conductive material (vias) between the antennas 1041 and/or by increasing the available surface area of connecting conductive material to increase skin-effect conduction. Similar results can be achieved by adding additional antenna elements 1041 on additional layers of a laminate antenna assembly 1040 (e.g., connected by multiple vias or otherwise connected as described herein). In some embodiments, multiple vias are added such that every 10 mOhm of reduced resistance achieves a transmission link gain of approximately 0.3 dB.

In some embodiments, antenna assembly 1040 comprises more than two antenna elements 1045, each neighboring pair separated by at least one substrate (e.g., a dielectric layer). For example, antenna assembly 1040 can comprise at least 3 layered antenna elements 1045, at least 4 layered antenna elements 1045, at least 5 layered antenna elements 1045, or at least 6 layered antenna elements 1045. Each neighboring pair of antenna elements 1045 can be connected by one or more vias 1056 between them. Antenna assembly 1040 can comprise multiple (e.g., 2, 3, 4 or more) layers of antenna elements 1045 such as to increase the collective surface area of the antenna and/or to lower its resistance (e.g., due to skin effect).

Figures 4E, 4F:
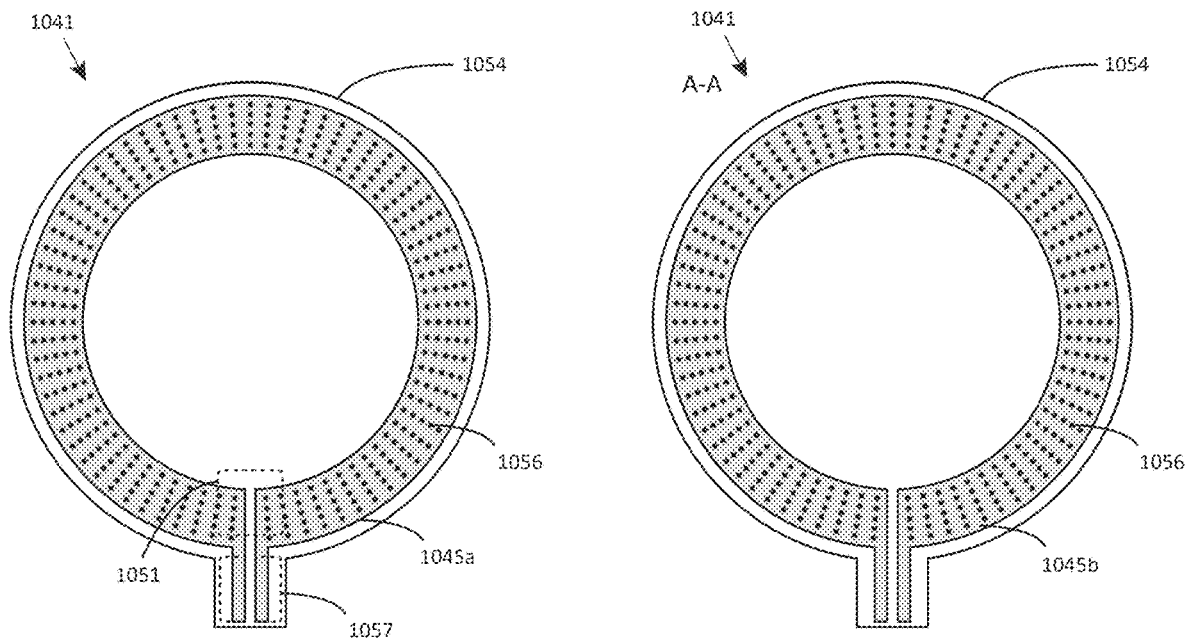
FIGS. 4E-4F are a top view and bottom view, respectively, of a laminate antenna assembly comprising multiple antenna elements and multiple connecting vias, consistent with the present inventive concepts.

Referring now to FIGS. 4E-F, a bottom view and a top view, respectively, of a laminate antenna assembly comprising multiple antenna elements and multiple connecting vias is illustrated, consistent with the present inventive concepts. In FIG. 4F, top layers (e.g., layers above section A-A of FIG. 4D) have been removed to illustrate antenna element 1045*b*. An antenna 1041 comprises a first antenna element 1045*a* (e.g., a first copper or other conductive trace) positioned on a bottom side of substrate 1054 and a second antenna element 1045*b* (e.g., a second copper or other conductive trace) positioned on a top side of substrate 1054. Antenna 1041 includes multiple vias 1056 (e.g., at least 10 vias, at least 50 vias, at least 100 vias, at least 500 vias, or at least 1000 vias that pass through substrate 1054) that reside within the width of the ring-shaped traces of antenna elements 1045*a* and 1045*b* to connect the two elements.

Antenna 1041 can further include conductive pad 1057, which includes one or more conductive pads located above antenna element 1045*b* (e.g., positioned on the top side of spacer 1043) for attaching antenna 1041 to a different component of external device 500 or implantable device 200 (e.g., for attaching to substrate 511 of external device 500 via connector 517). Antenna 1041 can further include components 1051 (e.g., also positioned on the top side of spacer 1043) which can be configured as a matching network for antenna 1041. In some embodiments, spacer 1043 and/or another substrate or layer of antenna 1041 comprises vias, such as to electrically connect trace layer 1055 to antenna elements 1045*a* and/or 1045*b*, and/or another electronic component of antenna 1041.

Figure 5A:
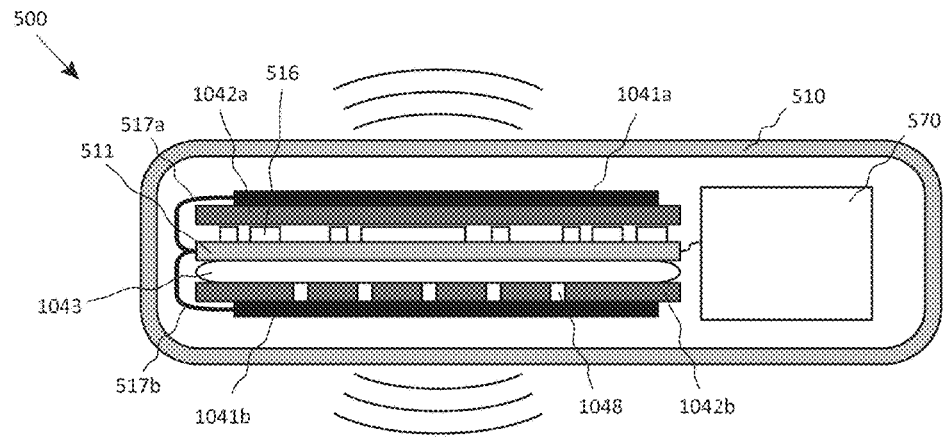
FIGS. 5A-5B are side sectional views of external devices, each including a shielded antenna assembly, consistent with the present inventive concepts.
Figure 5B:
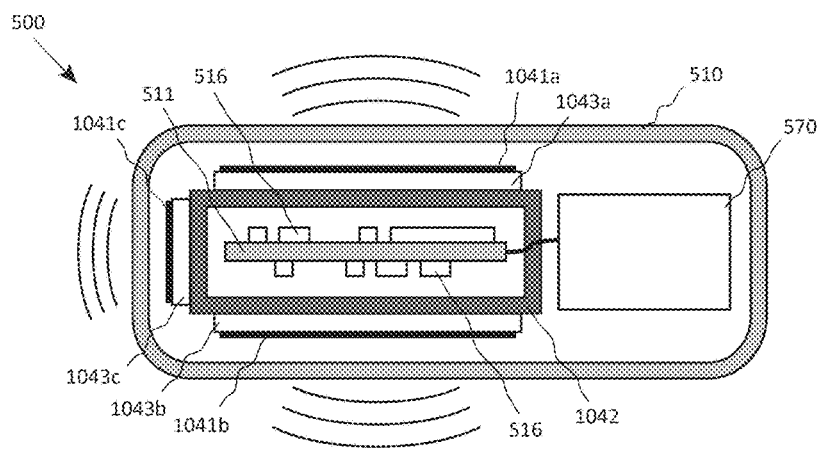

Referring now to FIGS. 5A-B, side sectional views of external devices, each including a shielded antenna assembly, are illustrated, consistent with the present inventive concepts. External device 500's of FIGS. 5A-B can be of similar construction and arrangement and include similar components to external device 500 described hereabove in reference to FIG. 1. Antenna assembly 1040 can be of similar construction and arrangement to any antenna assembly 1040 described herein. In some embodiments, antenna assembly 1040 includes multiple antennas 1041, such as are shown in FIGS. 5A-B. In these embodiments, one or more antennas 1041 can be configured to receive wireless power, such as to recharge power supply 570 (e.g., when power supply 570 comprises a rechargeable battery or capacitor).

In FIG. 5A, external device 500 comprises an antenna 540 comprising an antenna assembly 1040 including two antennas 1041, antennas 1041*a* and 1041*b* shown, and two shields 1042, shield 1042*a* and 1042*b* shown. Antenna assembly 1040 can be of similar construction and arrangement to any antenna assembly 1040 described herein. Antenna 1041*a* is positioned above substrate 511, with shield 1042*a* positioned between antenna 1041*a* and substrate 511. Antenna 1041*b* is positioned below substrate 511, with shield 1042*b* positioned between antenna 1041*b* and substrate 511. In the configuration and layout of antenna assembly 1040 shown in FIG. 5A, shield 1042*a* is positioned such than antenna 1041*a* is shielded from deleterious effects of components 516 and other electromagnetic field generating elements positioned below shield 1042*a*, and shield 1042*b* is positioned such that antenna 1041*b* is shielded from deleterious effects of components 516 and other electromagnetic field generating elements positioned above shield 1042*b*, each as described herein. Alternatively or additionally, this orientation improves transmissions (e.g., power and/or data transmissions) of antennas 1041*a* and 1041*b* to implantable device 200, also as described herein.

In FIG. 5B, external device 500 comprises an antenna 540 comprising an antenna assembly 1040 including three antennas 1041, antennas 1041*a*, 1041*b* and 1041*c* shown, and a shield 1042. Antenna 1041*a* is positioned above substrate 511, with a top portion of shield 1042 positioned between antenna 1041*a* and substrate 511. Antenna 1041*b* is positioned below substrate 511, with a bottom portion of shield 1042 positioned between antenna 1041*b* and substrate 511. Antenna 1041*c* is positioned to the left of substrate 511, with a side portion of shield 1042 positioned between antenna 1041*c* and substrate 511. In alternative embodiments, one or more of the top portion, bottom portion and/or side portion of shield 1042 comprises a separate discrete shield (e.g., a first shield 1042*a* positioned below antenna 1041*a*, a second shield 1042*b* positioned above antenna 1041*b*, and a third shield 1042*c* positioned to the right of antenna 1041*c*). In some embodiments, one or more spacers 1043 are included, such as spacers 1043*a-c* shown in FIG. 5B and positioned between antennas 1041*a-c*, respectively, and shield 1042. In the configuration and layout of antenna assembly 1040 shown in FIG. 5B, the top portion of shield 1042 is positioned such that antenna 1041*a* is shielded from deleterious effects of components 516 and other electromagnetic field generating elements positioned below the top portion of shield 1042, the bottom portion of shield 1042 is positioned such that antenna 1041*b* is shielded from deleterious effects of components 516 and other electromagnetic field generating elements positioned above the bottom portion of shield 1042, and the side portion of shield 1042 is positioned such that antenna 1041*c* is shielded from deleterious effects of components 516 and other electromagnetic field generating elements positioned to the right of the side portion of shield 1042, each shielding effect as described herein. Alternatively or additionally, this configuration of shield 1042 (including the three planar portions as shown in FIG. 5B or three separate shields 1042 positioned in the three planes) improves transmissions (e.g., power and/or data transmissions) of antennas 1041*a*, 1041*b* and 1041*c* to implantable device 200, also as described herein.

In some embodiments, an antenna assembly 1040 includes a shield 1042 with one or more holes or slots, holes 1048 shown in FIG. 5A, such as to reduce weight.

As described in reference to FIGS. 4 A-C and 5A, shield 1042 can comprise multiple shields and/or shields that lie on multiple planes that can be configured to shield one or more antennas 1041 from one or more electromagnetic field generating components positioned in multiple directions relative to each antenna 1041.

While the embodiments shown in FIGS. 4A-C and 5A include one or more shields included in an antenna assembly of an external device 500, similar antenna assemblies can be included in one or more implantable devices 200.

Figure 6:
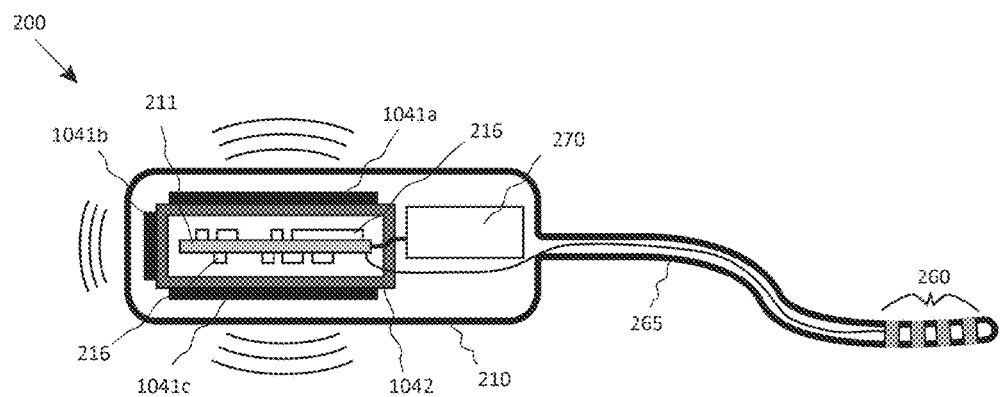
FIG. 6 is a side sectional view of an implantable device including a shielded antenna assembly, consistent with the present inventive concepts.

Referring now to FIG. 6, a side sectional view of an implantable device including a shielded antenna assembly is illustrated, consistent with the present inventive concepts. Implantable device 500 can be of similar construction and arrangement and include similar components to implantable device 200 described hereabove in reference to FIG. 1. Implantable device 200 comprises lead 265 including one or more functional elements 260 configured to stimulate tissue (e.g., one or more electrode-based or other stimulation energy delivering functional elements 260). Implantable device 200 further comprises housing 210, which can include one or more attachable portions which can be fixedly attached to each other via one or more attachment elements such as adhesive and/or via one or more attachment processes such as welding, such as to provide a sufficient seal to prevent a significant amount of contaminants from passing between the multiple housing 210 portions. Housing 210 surrounds multiple components and/or assemblies of implantable device 200, such as energy storage assembly 270 (e.g., including one or more batteries, capacitors or other energy storage components) and substrate 211. One or more electronic components 216 can be attached to substrate 211, and similarly electrically connected via one or more conductive traces of substrate 211 (e.g., when substrate 211 comprises one or more single or multiple layer printed circuit boards). Energy storage assembly 270 can be positioned (e.g., attached) on a top surface of substrate 211, or positioned at a separate location as shown, and can be electrically connected to one or more conductive traces of substrate 211.

Implantable device 200 can comprise an antenna 240 comprising one or more antennas, such as an antenna assembly 1040 comprising one, two, three, four or more antennas, such as the three antennas 1041*a-c* shown. Antenna assembly 1040 can comprise one or more shields, such as a rectangular cross section shield, shield 1042 shown. Each surface of shield 1042 is configured to shield one of antennas 1041*a-c* from components 216 positioned on substrate 211, as described herein. Alternatively or additionally, this configuration of shield 1042 improves transmissions (e.g., power and/or data transmissions) of antennas 1041*a-c*, also as described herein. In some embodiments, implantable device 200 comprises a single antenna 1041, or two antennas 1041, such as when implantable device 200 further comprises a single shield 1042, two shields 1042, or three or more shields 1042, which collectively provide shielding and/or improved transmission of the one or two antennas 1041.

Figure 7:
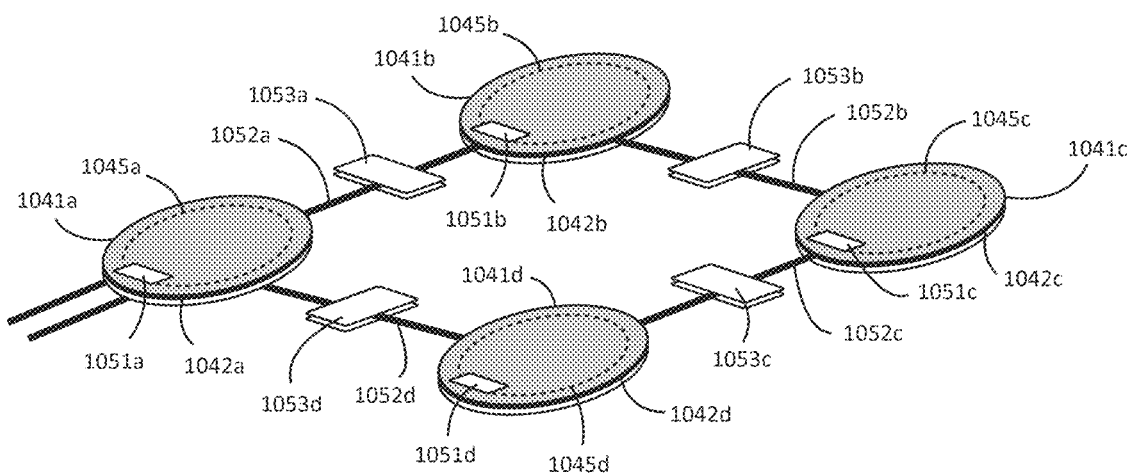
FIG. 7 is a perspective view of an antenna assembly comprising multiple antennas, consistent with the present inventive concepts.

Referring now to FIG. 7, a perspective view of an antenna assembly comprising multiple antennas is illustrated, consistent with the present inventive concepts. Antenna assembly 1040 of FIG. 7 can be included in external device 500 and/or implantable device 200 of system 10. Antenna assembly 1040 comprises two or more antennas 1041, such as the four antennas 1041*a-d* shown. Each antenna 1041*a-d* can comprise a receiving/transmitting portion, antenna element 1045. Antenna assembly 1040 can comprise one or more shields 1042, such as four shields 1042*a-d* which are positioned relatively concentrically about the four antennas 1041*a-d*, respectively. In an alternative embodiment, fewer than four shields 1042 are included, such as a single shield positioned relatively concentrically about the periphery defined collectively by the four antennas 1041*a-d*. In some embodiments, one or more of antennas 1041*a-d* comprises an antenna 1041 as described hereabove in reference to FIG. 1A or otherwise as described herein.

In some embodiments, two or more of the antennas 1041 are electrically connected, such as via a conductor, conductor 1052 (conductors 1052*a-d* shown connecting antennas 1041*a-d*). In these embodiments, one or more components 1053 (components 1053*a-d* shown) can also be electrically connected with the conductor 1052 (e.g., in series with conductor 1052 as shown). Each component 1053 can comprise one or more electrical components, such as components which include one or more capacitors or other impedance elements. In some embodiments, the one or more impedance elements can have their impedance dynamically adjusted, enabling phase and amplitude control of each antenna 1041 independently, such as to provide beam steering and/or power transfer optimization (e.g., to one or more receiving antennas 240 of an implantable device 200 positioned relatively proximate the array of antennas 1041). In some embodiments, component 1053 comprises one or more capacitors comprising silicon bulk capacitors, deep well trench capacitors, and/or other variable capacitors. Component 1053 can comprise one or more capacitors and bias control circuitry configured to modulate the impedance. In some embodiments, component 1053 comprises one or more high frequency transmission gate switches which can be configured to modify the connection scheme between antennas 1041 of the array, such as to adjust beam formation and/or adjust (e.g., optimize) power transfer (e.g., to one or more antennas 240 of an implanted device 200). In some embodiments, component 1053 can comprise one or more components integrated into a silicon wafer, such as to sense and control impedance of component 1053. In some embodiments, component 1053 (or other electronic circuitry of system 10) can comprise components including a microcontroller configured to measure and/or control impedance of component 1053 and/or other portions of antenna assembly 1040.

In some embodiments, antennas 1041*a-d* are mounted to a substrate, not shown but such as a substrate in which conductors 1052*a-d* are traces that are also mounted to the substrate and/or components 1053*a-d* that are also mounted to the substrate.

Figure 8:
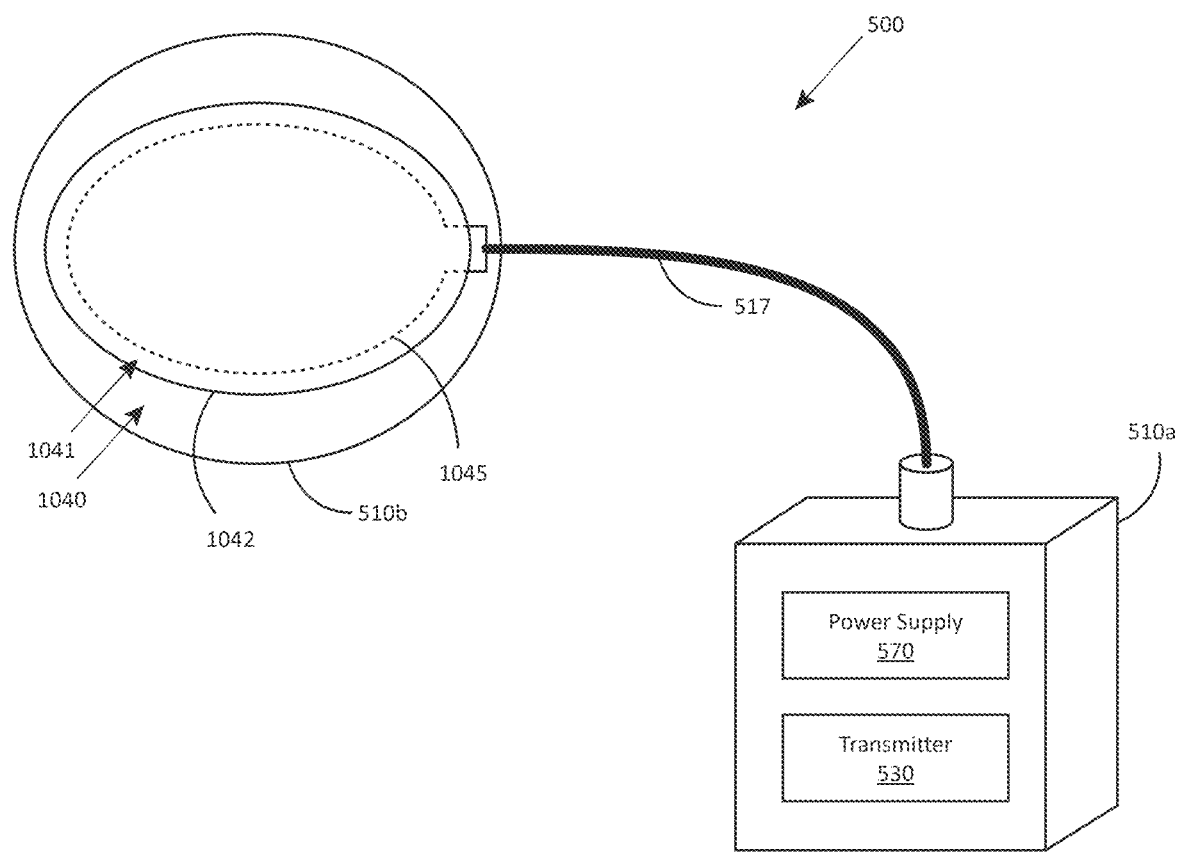
FIG. 8 is a perspective view of an external device comprising an attached antenna assembly, consistent with the present inventive concepts.

Referring now to FIG. 8, a perspective view of an external device comprising an attached antenna assembly is illustrated, consistent with the present inventive concepts. External device 500 comprises a housing 510 including two discrete portions, housing 510*a* and housing 510*b* shown. Housing 510*a* surrounds at least transmitter 530 and power supply 570, as described herein. Housing 510*b* surrounds antenna assembly 1040, also as described herein. Antenna assembly 1040 includes antenna 1041 which includes at least one antenna element 1045 (e.g., two or more antenna elements 1045 as described hereabove in reference to FIGS. 4D-F). Antenna assembly 1040 can further include at least one shielding element, shield 1042. Antenna assembly 1040 is electrically connected to transmitter 530 by connector 517 (e.g., a flexible or other connecting filament comprising one or more wires or otherwise as described herein). In some embodiments, antenna assembly 1040 further comprises one or more space-providing elements, not shown but such as spacer 1043 described herein.

External device 500 of FIG. 8 can be configured such that housing 510*b* is positioned on or at least proximate the patient's skin, such as to transfer power and/or data to a nearby implantable device 200 which has been implanted under the patient's skin. In this use, housing 510*a* can be positioned relatively away from the patient's skin, such as at a location on a belt or in a pocket of a patient-worn garment.

While the embodiments described hereabove have focused primarily on electrical and other stimulation systems, all medical apparatus including an implantable device that receives power and/or data from an external device should be considered within the spirit and scope of this application.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A medical apparatus for a patient, comprising:
   an external system configured to transmit one or more transmission signals, each transmission signal comprising at least power or data; and
   an implantable system configured to receive the one or more transmission signals from the external system;
   wherein the external system comprises a first external device comprising:
   an external antenna assembly configured to transmit a first transmission signal to the implantable system, the first transmission signal comprising at least power or data;
   an external transmitter configured to drive the external antenna assembly;
   an external power supply configured to provide power to at least the external transmitter; and
   an external controller configured to control the external transmitter; and
   wherein the implantable system comprises a first implantable device comprising:
   an implantable antenna assembly configured to receive the first transmission signal from the first external device;
   an implantable receiver configured to receive the first transmission signal from the implantable antenna assembly;
   at least one implantable functional element configured to interface with the patient;
   an implantable controller configured to control the at least one implantable functional element;
   an implantable energy storage assembly configured to provide power to an element selected from the group consisting of: the at least one implantable functional element; the implantable controller; the implantable receiver; and combinations thereof;
   and
   an implantable housing surrounding at least the implantable controller and the implantable receiver;
   wherein the external antenna assembly comprises:
   at least one external antenna; and
   at least one shielding element positioned between the at least one external antenna and at least one of the external power supply or the external controller, such that the at least one external antenna is on a first side of the at least one shielding element and the at least one of the external power supply or external controller is on a second side of the at least one shielding element opposite the first side;
   wherein the at least one shielding element is configured to reduce losses and/or loading effects caused by deleterious effects of the at least one external power supply or external controller;
   wherein the at least one shielding element comprises one or more electromagnetic absorptive materials and one or more conductive materials on the second side, and wherein the one or more electromagnetic absorptive materials and the one or more conductive materials are configured to increase shielding of the at least one shielding element,
   wherein the at least one shielding element comprises a material having a low magnetic loss tangent ($u''/u'$) at the operating frequency of the antenna transmission, wherein the magnetic loss tangent ($u''/u'$) is less than or equal to 0.025 at the operating frequency of the antenna transmission, and wherein the one or more conductive materials have a conductivity of less than or equal to 1e−3 S/m or 1e−5 S/m at the operating frequency.

2. The medical apparatus according to claim 1, wherein the at least one shielding element is configured to shield one or more of the external power supply, the external controller, and the external transmitter from undesired radiations from the external antenna.

3. The medical apparatus according to claim 1, wherein the at least one shielding element is configured to magnify a magnetic field of the external antenna assembly.

4. The medical apparatus according to claim 1, wherein the at least one shielding element comprises a hole and wherein the first external device comprises an electrical connection that passes through the hole.

5. The medical apparatus according to claim 1, wherein the at least one shielding element is configured to increase directivity of the external antenna assembly.

6. The medical apparatus according to claim 1, wherein the at least one shielding element is configured to limit a transmitting direction of the external antenna assembly.

7. The medical apparatus according to claim 1, wherein the first external device further comprises a spacer positioned between the at least one external antenna and the at least one shielding element.

8. The medical apparatus according to claim 7, wherein the spacer comprises a printed circuit board.

9. The medical apparatus according to claim 8, wherein the spacer comprises a thickness between 0.01 mm and 5 mm.

10. The medical apparatus according to claim 8, wherein the spacer comprises a non-conductive dielectric material.

11. The medical apparatus according to claim 1, wherein a periphery of the at least one shielding element fully covers a periphery of the at least one external antenna.

12. The medical apparatus according to claim 11, wherein the periphery of the at least one shielding element extends beyond the periphery of the at least one external antenna.

13. The medical apparatus according to claim 1, wherein the first external device comprises electronic componentry configured as a matching network.

14. The medical apparatus according to claim 13, wherein the at least one shielding element comprises a cutout and the electronic componentry extends into the cutout.

15. The medical apparatus according to claim 13, wherein the electronic componentry includes a tuning element.

16. The medical apparatus according to claim 1, wherein the at least one external antenna is configured to deliver transmissions with an operating frequency above 1 Mhz.

17. The medical apparatus according to claim 1, wherein the at least one external antenna is configured to deliver transmissions with an operating frequency above 10 MHz.

18. The medical apparatus according to claim 1, wherein the at least one shielding element comprises high frequency ferrite.

19. The medical apparatus according to claim 1, wherein the at least one shielding element comprises a material selected from the group consisting of: electromagnetically absorptive material; RF absorptive material; conductive material; and combinations thereof.

20. The medical apparatus according to claim 1, wherein the at least one shielding element is configured to shield one or more electronic components surrounding the at least one external antenna.

21. The medical apparatus according to claim 1, wherein the external device further comprises a housing, wherein the at least one shielding element, the external antenna, the external power supply, and the external controller are positioned within the housing of the external device.

22. The medical apparatus according to claim 1, wherein both the external power supply and the external controller are on the second side of the at least one shielding element.

* * * * *